US012603152B2

(12) United States Patent
Kermani et al.

(10) Patent No.: US 12,603,152 B2
(45) Date of Patent: Apr. 14, 2026

(54) METHODS AND APPLICATIONS OF GENE FUSION DETECTION IN CELL-FREE DNA ANALYSIS

(71) Applicant: GUARDANT HEALTH, INC., Redwood City, CA (US)

(72) Inventors: Bahram Ghaffarzadeh Kermani, Los Altos, CA (US); Mohammad Reza Mokhtari, San Lorenzo, CA (US)

(73) Assignee: Guardant Health, Inc., Palo Alto, CA (US)

( * ) Notice: Subject to any disclaimer, the term of this patent is extended or adjusted under 35 U.S.C. 154(b) by 775 days.

(21) Appl. No.: 15/766,733

(22) PCT Filed: Oct. 10, 2016

(86) PCT No.: PCT/US2016/056314
§ 371 (c)(1),
(2) Date: Apr. 6, 2018

(87) PCT Pub. No.: WO2017/062970
PCT Pub. Date: Apr. 13, 2017

(65) Prior Publication Data
US 2018/0300449 A1     Oct. 18, 2018

Related U.S. Application Data

(60) Provisional application No. 62/239,879, filed on Oct. 10, 2015.

(51) Int. Cl.
| | |
|---|---|
| *G16B 30/10* | (2019.01) |
| *C12Q 1/686* | (2018.01) |
| *C12Q 1/6869* | (2018.01) |
| *C12Q 1/6874* | (2018.01) |
| *C12Q 1/6886* | (2018.01) |
| *G16B 30/00* | (2019.01) |
| *G16B 40/00* | (2019.01) |

(52) U.S. Cl.
CPC ............. *G16B 30/10* (2019.02); *C12Q 1/686* (2013.01); *C12Q 1/6869* (2013.01); *C12Q 1/6874* (2013.01); *C12Q 1/6886* (2013.01); *G16B 30/00* (2019.02); *G16B 40/00* (2019.02)

(58) Field of Classification Search
None
See application file for complete search history.

(56) References Cited

U.S. PATENT DOCUMENTS

| | | | |
|---|---|---|---|
| 6,586,177 | B1 | 7/2003 | Shuber |
| 6,849,403 | B1 | 2/2005 | Shuber |
| 7,406,385 | B2 | 7/2008 | Sorenson |
| 7,410,764 | B2 | 8/2008 | Gocke et al. |
| 7,727,720 | B2 | 6/2010 | Dhallan |
| 7,811,757 | B2 | 10/2010 | Shuber |
| 7,838,647 | B2 | 11/2010 | Hahn et al. |
| 7,935,487 | B2 | 5/2011 | Gocke et al. |
| 8,697,408 | B2 | 4/2014 | Kucera et al. |
| 8,865,410 | B2 | 10/2014 | Shendure et al. |
| 9,340,830 | B2 | 5/2016 | Lipson et al. |
| 2008/0161420 | A1 | 7/2008 | Shuber |
| 2010/0196898 | A1 | 8/2010 | Sugarbaker et al. |
| 2011/0245482 | A1 | 10/2011 | Hahn et al. |
| 2012/0165222 | A1 | 6/2012 | Porreca et al. |
| 2012/0191367 | A1 | 7/2012 | Stuelpnagel et al. |
| 2014/0011694 | A1 | 1/2014 | Couronne |
| 2014/0296081 | A1 | 10/2014 | Diehn et al. |
| 2014/0336943 | A1 | 11/2014 | Pellini et al. |
| 2014/0357500 | A1 | 12/2014 | Vigneault et al. |
| 2015/0024950 | A1 | 1/2015 | Bielas et al. |
| 2015/0044687 | A1 | 2/2015 | Schmitt et al. |
| 2015/0087535 | A1 | 3/2015 | Patel |
| 2015/0142328 | A1 | 5/2015 | Jung et al. |
| 2015/0329917 | A1 | 11/2015 | Shuber |
| 2015/0344970 | A1 | 12/2015 | Vogelstein et al. |
| 2015/0366866 | A1 | 12/2015 | Ali et al. |
| 2016/0032396 | A1 | 2/2016 | Diehn et al. |
| 2017/0051347 | A1 | 2/2017 | Vogelstein et al. |

(Continued)

FOREIGN PATENT DOCUMENTS

| | | |
|---|---|---|
| EP | 3169804 A1 | 5/2017 |
| EP | 3125936 B1 | 5/2019 |

(Continued)

OTHER PUBLICATIONS

Tucker et al. Tucker et al. Massively Parallel Sequencing: The Next Big Thing in Genetic Medicine Am J Hum Genet. Aug. 14, 2009; 85(2): 142-154. doi: 10.1016/j.ajhg.2009.06.022.*

Daniel C. Koboldt, Massively Parallel Sequencing Approaches for Characterization of Structural Variation, Methods Mol Biol. 2012; 838: 369-384. doi: 10.1007/978-1-61779-507-7_18.*

Rausch et al. DELLY: structural variant discovery by integrated paired-end and split-read analysis Bioinformatics vol. 28 ECCB 2012, pp. i333-i339 doi: 10.1093/bioinformatics/bts378.*

Liu et al. Structural variation discovery in the cancer genome using next generation sequencing: Computational solutions and perspectives Oncotarget vol. 6, No. 8, Mar. 8, 2015.*

(Continued)

*Primary Examiner* — Joseph Woitach

(74) *Attorney, Agent, or Firm* — Indhu Kanakaraj

(57) ABSTRACT

Systems and methods are disclosed for determining gene fusion by determining a fused read containing sequencing data of a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion.

15 Claims, 12 Drawing Sheets

(56) References Cited

U.S. PATENT DOCUMENTS

| | | | |
|---|---|---|---|
| 2017/0073774 | A1 | 3/2017 | Lo et al. |
| 2017/0159120 | A1 | 6/2017 | Eijk et al. |
| 2018/0251848 | A1 | 9/2018 | Diehn et al. |
| 2019/0185910 | A1 | 6/2019 | Li et al. |
| 2019/0241974 | A1 | 8/2019 | Woodhouse et al. |
| 2019/0241975 | A1 | 8/2019 | Woodhouse et al. |
| 2019/0241977 | A1 | 8/2019 | Woodhouse et al. |
| 2019/0241978 | A1 | 8/2019 | Woodhouse et al. |

FOREIGN PATENT DOCUMENTS

| | | |
|---|---|---|
| WO | 2011087760 A2 | 7/2011 |
| WO | 2011091046 A1 | 7/2011 |
| WO | 2013142389 A1 | 9/2013 |

OTHER PUBLICATIONS

Korbel et al. Paired-End Mapping Reveals Extensive Structural Variation in the Human Genome Science. Oct. 19, 2007; 318(5849): 420-426. doi: 10.1126/science.1149504.*

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Lanman, R.B. et al. "Analytical and Clinical Validation of a Digital Sequencing Panel for Quantitative, Highly Accurate Evaluation of Cell-Free Circulating Tumor DNA" PLoS (2015) 10(10):e0140712 doi: 10.1371/journal.pone.0140712.

Newman, et al. An ultrasensitive method for quantitating circulating tumor DNA with broad patient coverage. Nat Med. May 2014; 20(5):548-54. doi: 10.1038/nm.3519. Epub Apr. 6, 2014.

Odegaard, J.I. et al. "Validation of a Plasma-Based Comprehensive Cancer Genotyping Assay Utilizing Orthogonal Tissue- and Plasma-Based Methodologies" Clin Canc Res (2018) 24(15):3539-3549.

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Phallen, J. et al. "Direct detection of early-stage cancers using circulating tumor DNA" Sci Trans Med (2017) vol. 9, Issue 403, eaan2415DOI: 10.1126/scitranslmed.aan2415.

Villaflor, V. et al. "Biopsy-free circulating tumor DNA assay identifies actionable mutations in lung cancer" Oncotarget (2016) 7(41):66880-66891.

Zill, O.A. et al. "The Landscape of Actionable Genomic Alterations in Cell-Free Circulating Tumor DNA from 21,807 Advanced Cancer Patients" Clin Canc Res (2018) 24(15):3528-3538.

Vasyukhin, V. et al., "K-Ras Point Mutations in the Blood Plasma DNA of Patients with Colorectal Tumors" Challenges of Modern Medicine, 141-150 (Verna and Shamoo eds, 1994).

Wagle, N. et al., "High-throughput Detection of actionable Genomic alterations in clinical tumor samples by targeted, Massively Parallel sequencing," Cancer Discov. 2012, (2)1:82-93.

Wang, Y. et al., "Detection of somatic mutations and HPV in the saliva and plasma of patients with head and neck squamous cell carcinomas," Sci. Transl. Med. 2015, 7(293):293ra104.

Wang, Y. et al., "Detection of tumor-derived DNA in cerebrospinal fluid of patients with primary tumors of the brain and spinal cord," Proc. Natl. Acad. Sci. USA 2015, 112(31), 9704-9709.

Wang, Y. et al., "Diagnostic potential of tumor DNA from ovarian cyst fluid," eLife 2016, 5:e15175.

Wheeler, D.A. et al., "The complete genome of an individual by massively parallel DNA sequencing," Nature 2008, 452(7189), 872-876.

Williford, A. et al., "Gene Fusion," eLS 2013, 1-8.

"Control," Oxford Dictionary of Biochemistry and Molecular Biology (2d ed. 2006), 143.

Ajay, S.S. et al., "Accurate and comprehensive sequencing of personal genomes," Genome Res. 2011, 21(9), 1498-1505.

Albert, T.J. et al., "Direct selection of human genomic loci by microarray hybridization," Nat. Methods 2007, 4(11), 903-905.

Arneson, N. et al., "Whole-Genome Amplification by Adaptor-Ligation PCR of Randomly Sheared Genomic DNA (PRSG)," CSH Protocols, 2008, 3(1).

Bentley, D.R. et al., "Accurate Whole Human Genome Sequencing using Reversible Terminator Chemistry," Nature, 2008, 456(7218):53-59.

Bettegowda et al., "Detection of Circulating Tumor DNA in Early-and Late-Stage Human Malignancies," Sci. Transl. Med. 2014, 6(224):224ra24.

Bianchi, D.W. et al. "Genome-Wide Fetal Aneuploidy Detection by Maternal Plasma DNA Sequencing," Obstetrics & Gynecology, (2012) 119(5), 1-12.

Bryzgunova, O. et al., "A reliable method to concentrate circulating DNA," Analytical Biochem., 2010, 408:354-356.

CASAVA v1.8.2 User Guide http://gensoft.pasteur.fr/docs/casava/1.8.2/CASAVA_1_8_2_UG_15011196C.pdf (Oct. 2011).

Ding, L. et al., "Analysis of next-generation genomic data in cancer: accomplishments and challenges," Hum. Mol. Genet. 2010 19(R2), R188-R196.

Duncan, D.L. et al. "Next-Generation Sequencing in the Clinical Laboratory" Diagnostic Molecular Pathology: A Guide to Applied Molecular Testing 25-33 (Coleman and Tsongalis eds., 1st ed. 2016).

Gordon, D.J. et al., "Causes and consequences of aneuploidy in cancer," Nat. Rev. Genet. 2012 13(3), 189-203.

Hall, A., Short-Read DNA Sequence Alignmnet with Custom Designed FPGA-based Hardware, Thesis 2010.

Ilumina "Multiplexed Sequencing with Illumina Genome Analyzer System" https://www.illumina.com/Documents/products/datasheets/datasheet_sequencing_multiplex.pdf (Dec. 2008).

IPR2019-00130, Preliminary Response to Petition for Inter Partes Review U.S. Pat. No. 9,598,731, filed Mar. 6, 2019.

Jiang, H. et al., "SeqMap: mapping massive amount of oligonucleotides to the genome," Bioinformatics 2008, 24(20):2395-2396.

Kao, W-C. et al., "BayesCall: A model-based base-calling algorithm for high-throughput short-read sequencing," Genome Res. 2009 19(10), 1884-1895.

Kennedy, S.R. et al., "Detecting ultralow-frequency mutations by Duplex Sequencing," Nat. Protoc. 2014, 9(11), 2586-2606.

Kinde, I. et al., "Evaluation of DNA from the Papanicolaou Test to Detect Ovarian and Endometrial Cancers," Sci. Transl. Med. 2013, 5(167): 167ra4.

Kinde, I. et al., "FAST-SeqS: a simple and efficient method for the detection of aneuploidy by massively parallel sequencing," PLoS One 2012, 7(7), e41162.

Kircher, M. et al., "Improved base calling for the Illumina Genome Analyzer using machine learning strategies," Genome Biol. 2009, 10(8), R83.

Kirsch, S. et al. "Sequence error storms and the landscape of mutations in cancer," Proc. Natl. Acad. Sci. USA 2012, 109(36), 14289-14290.

Koboldt, D.C.et al., "The next-generation sequencing revolution and its impact on genomics," Cell 2013, 155(1), 27-38.

Korbel, J.O. et al., "Paired-end mapping reveals extensive structural variation in the human genome," Science 2007, 318(5849), 420-426.

Krimmel, J.D. et al., "Ultra-deep sequencing detects ovarian cancer cells in peritoneal fluid and reveals somatic TP53 mutations in noncancerous tissues," Proc. Natl. Acad. Sci. USA 2016, 113(21), 6005-6010.

Ledergerber, C. et al., "Base-calling for next-generation sequencing platforms," Brief Bioinform. 2011 12(5), 489-497.

Li, H. et al., "Fast and accurate short read alignment with Burrows-Wheeler transform," Bioinformatics 2009, 25(14), 1754-1760.

Liang, K-C. et al., "Bayesian basecalling for DNA sequence analysis using hidden Markov models," IEE/ACM Trans. Comput. Biol. Bioinform. 2007 4(3), 430-440.

Liao, G.J.W. et al., "Targeted massively parallel sequencing of maternal plasma DNA permits efficient and unbiased detection of fetal alleles," Clin. Chem. 2011, 57(1), 92-101.

(56)                  References Cited

OTHER PUBLICATIONS

Lo, Y.M.D et al., "Quantitative analysis of fetal DNA in maternal plasma and serum: implications for noninvasive prenatal diagnosis," Am. J. Hum. Genet. 1998, 62(4), 768-775.

Lo, Y.M.D. et al. "Maternal Plasma DNA Sequencing Reveals the Genome-Wide Genetic and Mutational Profile of the Fetus," Sci Transl Med (2010) 2(61):1-13.

Lohman, G. "Efficient Adaptor Ligation for the Preparation of dsDNA Libraries using the Blunt/TA Ligase Master Mix" New England BioLabs Application Note.

Lunter, G. et al., "Stampy: A statistical algorithm for sensitive and fast mapping of Illumina sequence reads," Genome Res. 2011, 21(6):936-939.

Mamanova, L. et al., "Target-enrichment strategies for next-generation sequencing," Nat. Methods 2010, 7(2), 111-118.

Mckernon, K.J. et al., "Sequence and structural variation in a human genome uncovered by short-read, massively parallel ligation sequencing using two-base encoding," Genome Res. 2009, 19(9), 1527-1541.

Meyer, M. et al. "Illumina sequencing library preparation for highly multiplexed target capture and sequencing," Cold Spring Harb. Protoc. 2010, (6), prot5448.

Ng, S.B., et al., "Targeted capture and massively parallel sequencing of 12 human exomes," Nature 2009, 461(7261), 272-276.

Parkinson, N.J. et al., "Preparation of high-quality next-generation sequencing libraries from picogram quantities of target DNA," Genome Res. 2012, 22(1), 125-133.

Quinlan, A.R. et al., "Pyrobayes: an improved base caller for SNP discovery in pyrosequences," Nat. Methods 2008 5(2), 179-181.

Redon, R. et al., "Global variation in copy number in the human genome," Nature 2006 444(7118), 444-454.

Rizzo, J.M. et al. "Key Principles and Clinical Applications of 'Next Generation' DNA Sequencing," Cancer Prev. Res., (2012) 5, 887-900.

Sausen, M. et al. "Integrated genomic analyses identify ARID1A and ARID1B alterations in the childhood cancer neuroblastoma", Nature Genetics 2013, 45(1), 12-17.

Schweiger et al., "Genome-wide massively parallel sequencing of formaldehyde fixed-paraffin embedded (FFPE) tumor tissues for copy-number- and mutation-analysis," PLoS One 2009, 4(5), e5548.

Shendure, J. et al. "Next-generation DNA sequencing," Nat. Biotechnol. 2008 26(10), 1135-1145.

Stein, et al. "The case for cloud computing in genome informatics", Genome Biol. 2010; 11 (5):207. Epub May 5, 2010.

Tie, J. et al., "Circulating tumor DNA analysis detects minimal residual disease and predicts recurrence in patients with stage II colon cancer," Sci. Transl. Med. 2016, 8(346):346ra92.

U.S. Appl. No. 61/613,413 ("Schmitt '413 provisional")Sch.

U.S. Appl. No. 61/625,319 ("Schmitt '319 provisional").

Heng Li. Aligning Sequence Reads, Clone Sequences and Assembly Contigs with BWA-MEM. bRAOD Institute of Harvard And mit. vol. 00 No. 00; May 26, 2013. pp. 1-3.

Wang, Q. et al. "Application of next generation sequencing to human gene fusion detection: computational tools, features and perspectives" Briefings in Bioinformatics (2012) 14(4):506-519.

Zhang, J. et al. "Integrate: gene fusion discovery using whole genome and transcriptome data" Genome Res (2016) 26(1):108-18. doi: 10.1101/gr. 186114.114. Epub Nov. 10, 2015.

Chiang, et al.; SpeedSeq: Ultra-fast Personal Genome Analysis and Interpretation; Author Manuscript; Nat Methods; Oct. 2015; pp. 1-12.

Exam Report in European Patent Application No. 20163383.1, dated Oct. 5, 2023.

Layer, et al.; Lumpy: A Probabilistic Framework for Structural Variant Discovery; Genome Biology; 2014; pp. 1-19.

International search report and written opinion dated Aug. 3, 2018 for PCT/US2018/033553.

Kwon, S. et al. "CASPER: context-aware scheme for paired-end reads from high-throughput amplicon seqencing" BMC Bioinformatics (2014) 15(Suppl 9):S10 (11 pages).

Li, H. et al. "A survey of sequence alignment algorithms for next-generation sequencing" Briefings In Bioinformatics (2010) 2(5):473-483.

Marco-Sola, S. "Efficient Approximate String Matching Techniques for Sequence Alignment" Thesis, Universitat Politecnica de Catalunya (2017).

Wu, T-L. et al. "Cell-free DNA: measurement in various carcinomas and establishment of normal reference range" Clin Chim Acta (2002) 321:77-87.

Masunaga, N. et al. "Highly sensitive detection of ESR1 mutations in cell-free DNA from patients with metastatic breast cancer using molecular barcode sequencing" Breast Cancer Res & Treatment (2017) 167:49-58.

Murtaza, M. et al. "Non-invasive analysis of acquired resistance to cancer therapy by sequencing of plasma DNA" Nature (May 2013) 497(7447):108-112.

Newman, A. et al. "Integrated digital error suppression for improved detection of circulating tumor DNA" Nature Biotech (2016) 34(5):547-555.

Shea, M. et al. "Lazarus-Type Response to Crizotinib in a Patient with Poor Performance Status and Advanced MET Exon 14 Skipping Mutation-Positive Lung Adenocarcinoma" J Thoracic Oncology (2016) 16(7): e81-e82.

Zhang, J. et al. "PEAR: a fast and accurate Illumina Paired-End reAd mergeR" Bioinformatics (2014) 30(5):614-620.

\* cited by examiner

FIG. 1

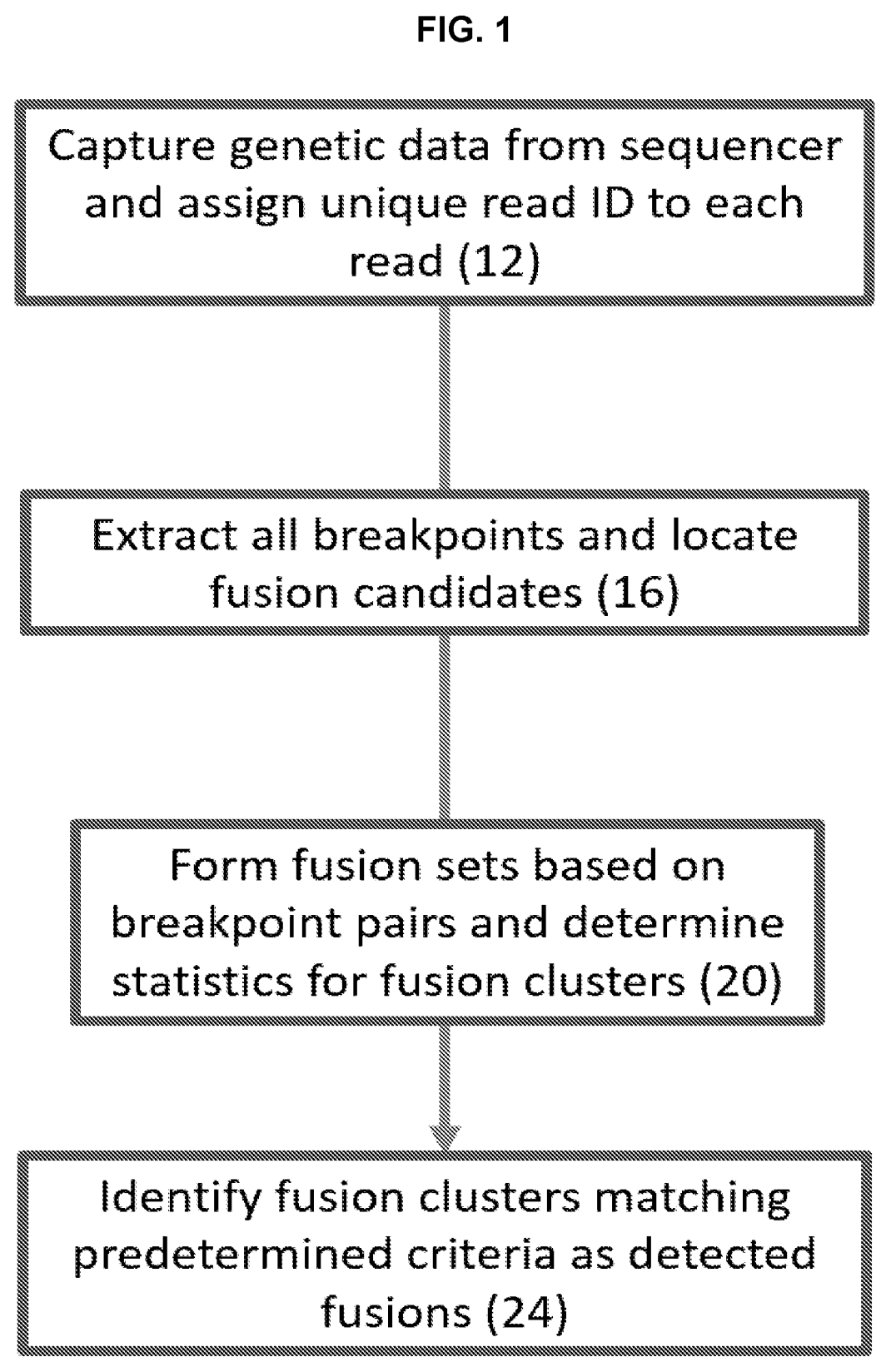

Capture genetic data from sequencer and assign unique read ID to each read (12)

Extract all breakpoints and locate fusion candidates (16)

Form fusion sets based on breakpoint pairs and determine statistics for fusion clusters (20)

Identify fusion clusters matching predetermined criteria as detected fusions (24)

Chromosome A:
  Breakpoint A1:  Fused Reads 1, 4, 3, 6 = four
  Breakpoint A2:  Fused Reads 2, 5 = two
    First Gene Fusion Breakpoint Call:  A1

Chromosome B:
  Breakpoint B1:  Fused Reads 1, 4, 2, 5 = four
  Breakpoint B2:  Fused Reads 3, 6 = two
    Second Gene Fusion Breakpoint Call:  B1

Gene Fusion Breakpoint pair:  A1-B1

Breakpoint Sets

| | | | | |
|---|---|---|---|---|
| A1 | 1 | 3 | 4 | 6 |
| A2 | 2 | 5 | | |
| A3 | 7 | | | |
| B1 | 1 | 2 | 5 | 6 |
| B2 | 3 | 4 | | |
| B3 | 7 | | | |

↓

Breakpoint Pairs

| | | |
|---|---|---|
| A1-B1 | 1 | 6 |
| A1-B2 | 3 | 4 |
| A1-B3 | — | |
| A2-B1 | 2 | 5 |
| A2-B2 | — | |
| A2-B3 | — | |
| A3-B1 | — | |
| A3-B2 | — | |
| A3-B3 | 7 | |

↓

Clusters within predetermined distance: A1-B1, A1-B2, A2-B1,

↓

Fusion Breakpoints (Voting): A1-B1

METHODS AND APPLICATIONS OF GENE FUSION DETECTION IN CELL-FREE DNA ANALYSIS

CROSS-REFERENCE

This application is a national-stage application of PCT application No. PCT/US2016/056314, filed October 10. 2016, which claims the benefit of U.S. Provisional Application No. 62/239,879, filed Oct. 10, 2015, each of which application is incorporated herein by reference in its entirety.

BACKGROUND OF THE INVENTION

Cancerous cells may have chromosomes that are fused together. If such a chromosome is sequenced, it will generate reads that can be mapped into two different zones (on the same or different chromosomes) of the genome. Gene fusion plays a role in the evolution of gene architecture. Duplication, sequence divergence, and recombination are the major contributors at work in gene evolution. When gene fusion happens in non-coding sequence region, it can lead to the misregulation of the expression of a gene now under the control of the cis-regulatory sequence of another gene. If it happens in coding sequences, gene fusion can cause the assembly of a new gene, allowing the appearance of new functions by adding peptide modules into a multi domain protein.

Chromosome banding analysis, fluorescence in situ hybridization (FISH), and reverse transcription polymerase chain reaction (RT-PCR) are common methods employed at diagnostic laboratories. These methods all have their distinct shortcomings due to the very complex nature of cancer genomes. Recent developments such as high-throughput sequencing and custom DNA microarrays bear promise of introduction of more efficient methods, but are still inadequate. High-throughput genome sequencing technologies have been used as a research tool and are currently being introduced in the clinics, and in the future of personalized medicine, whole genome sequence data may be an important tool to guide therapeutic intervention.

SUMMARY OF THE INVENTION

In one aspect, systems and methods are disclosed for determining gene fusion by determining a fused read containing sequencing data of at least a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion.

In one aspect, the present disclosure provides a method for processing genetic sequence read data from a sample, the method comprising: determining a fused read containing sequencing data of at least a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion.

In some embodiments, the method comprises assigning a unique molecule or read identifier (read ID) to each read. In some embodiments, the method comprises clipping each mapped portion of the reads from one or both sides. In some embodiments, the breakpoints are independent of the reads in identity and are identified by a sign, a chromosome and a position. In some embodiments, the breakpoints keep statistics including a number of reads and molecules that are clipped or split at the breakpoint, and a number of wild-type reads and molecules that pass over the breakpoint. In some embodiments, the method comprises selecting every two mapped read portions with common read IDs that belong to two breakpoints with appropriate signs as a potential fusion candidate. In some embodiments, the potential fusion candidate location in the original read before mapping shows the read portion as originally located next to each other. In some embodiments, the method comprises checking if read portions are mapped on one strand for differences in the breakpoints' signs. In some embodiments, the method comprises tracking fusion set statistics.

In some embodiments, the fusion set statistics are breakpoint IDs, number of molecules, or reads that are contained in the set. In some embodiments, the method comprises grouping fusion sets with similar breakpoints in a fusion cluster. In some embodiments, the similar breakpoints are breakpoints no more than 5 nucleotides, no more than 10 nucleotides or no more than 25 nucleotides apart. In some embodiments, the method comprises defining a fusion cluster between two regions in in the genome. In some embodiments, the method comprises determining for the fusion cluster a number of fused molecules for each partner. In some embodiments, the method comprises determining for the fusion cluster the number of fused reads for each partner. In some embodiments, the method comprises determining for the fusion cluster a number of wild-type molecules for each partner. In some embodiments, the method comprises determining for the fusion cluster a number of wild-type reads or molecules for each partner. In some embodiments, the method comprises determining for the fusion cluster a fusion percentage for each partner as a ratio of fused molecules over total molecule for each partner. In some embodiments, the total molecule comprises wild-type and clipped components. In some embodiments, the method comprises determining for the fusion cluster gene information for each partner. In some embodiments, the method comprises determining a downstream gene of the fusion cluster. In some embodiments, the criteria comprises having more than one molecule in the cluster or having at least a molecule with both Watson and Crick strands.

In one aspect, the present disclosure provides a system to analyze genetic information, comprising a DNA sequencer; a processor coupled to the DNA sequencer, the processor running computer code to process genetic sequence read data from a sample, the computer code comprising instructions for: determining a fused read containing sequencing data of a portion of a fused chromosome DNA molecule; determining at least a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion.

In one aspect, the present disclosure provides a method comprising: sequencing DNA molecules with a DNA sequencer to generate a collection of sequences; mapping the collection of sequences to a reference genome; identifying fused reads from the mapped collection, wherein a fused read contains sub-sequences, wherein a first sub-sequence maps to a first genetic locus and a second sub-sequence maps to a second, distinct genetic locus; for each fused read, identifying a first breakpoint at the first genetic locus and a second breakpoint at the second genetic locus, wherein a breakpoint is a point on the reference genome where a sequence of a fused read is clipped, and wherein the first and second breakpoints form a breakpoint pair; generating sets of fused reads, each set comprising fused reads having the same breakpoint pair; clustering sets of fused reads, wherein each cluster is formed from sets of fused reads having first breakpoints within a first predetermined nucleotide distance and second breakpoints within a second predetermined nucleotide distance; and determining a gene fusion for one or more clusters, wherein a gene fusion for a cluster has, as a first fusion gene breakpoint, a breakpoint selected from the first breakpoints in the cluster and, as a second fusion gene breakpoint, a breakpoint selected from the second breakpoints in the cluster, and wherein the first and second fusion gene breakpoints are each selected based on selection criteria.

In some embodiments, the distinct genetic loci are located on different chromosomes or on different genes of the same chromosome. In some embodiments, the first and second predetermined distances are each no more than 5 nucleotides, no more than 10 nucleotides or no more than 25 nucleotides. In some embodiments, the selection criteria include the breakpoint having the most fused reads in the cluster. In some embodiments, the method comprises determining a gene fusion for a plurality of gene clusters.

In one aspect, the present disclosure provides a method comprising: sequencing a plurality of DNA molecules with a DNA sequencer; tagging each of the plurality of sequences molecules with an identifier; mapping each tagged sequence to a reference genome; identifying clipped reads from the mapped tagged sequences, wherein a clipped read is a tagged sequence containing a mapped portion and a clipped portion, wherein the mapped portion maps to a genetic locus and the clipped portion does not map to the genetic locus; determining a breakpoint of each clipped read, wherein a breakpoint is a point on the reference genome where a sequence of a clipped read is clipped; creating breakpoint sets, each breakpoint set comprising identifiers of clipped reads having the same breakpoint; creating sets of breakpoint pairs by comparing pairs of breakpoint sets, each set of breakpoint pairs including identifiers present in both members of a compared pair of breakpoint sets; clustering sets of breakpoint pairs, wherein each cluster includes sets of breakpoint pairs having a first breakpoint of the pair within a first predetermined genetic distance and a second breakpoint of the pair within a second predetermined genetic distance; and determining a gene fusion for one or more of the clusters, wherein a gene fusion for a cluster has, as a first fusion gene breakpoint, a breakpoint selected from the first breakpoints in the cluster and, as a second fusion gene breakpoint, a breakpoint selected from the second breakpoints in the cluster, and wherein the first and second fusion gene breakpoints are each selected based on a selection criteria. In some embodiments, the selection criteria include the breakpoint having the most fused reads in the cluster.

In one aspect, the present disclosure provides a method for identifying a fusion gene breakpoint, the method comprising: determining a fused read containing sequencing data of at least a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; identifying each fusion cluster meeting a predetermined criterion as a gene fusion, and identifying a breakpoint of the gene fusion as the fusion gene breakpoint.

In one aspect, the present disclosure provides a method for diagnosing a condition in a subject, the method comprising: determining a fused read containing sequencing data of at least a portion of a fused chromosome DNA molecule; determining a predetermined point on the genome with least one mapped portion of the fused read clipped at the predetermined point (a breakpoint); identifying two mapped read portions from two breakpoints (breakpoint pair) as a potential fusion candidate; creating one or more fusion sets based on breakpoint pairs and clustering the fusion sets into one or more fusion clusters; and identifying each fusion cluster meeting a predetermined criterion as a gene fusion, wherein said gene fusion is indicative of the condition.

In some embodiments, the condition is a cancer. In some embodiments, the cancer is selected from the group consisting of: a hematological cancer, a sarcoma, and a prostate cancer. In some embodiments, the method further comprises administering a treatment to the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 diagrams an exemplary process for detecting gene fusion.

FIGS. 9A-9C show exemplary illustrations of the gene fusion detection process.

DETAILED DESCRIPTION OF THE INVENTION

Figure 2:
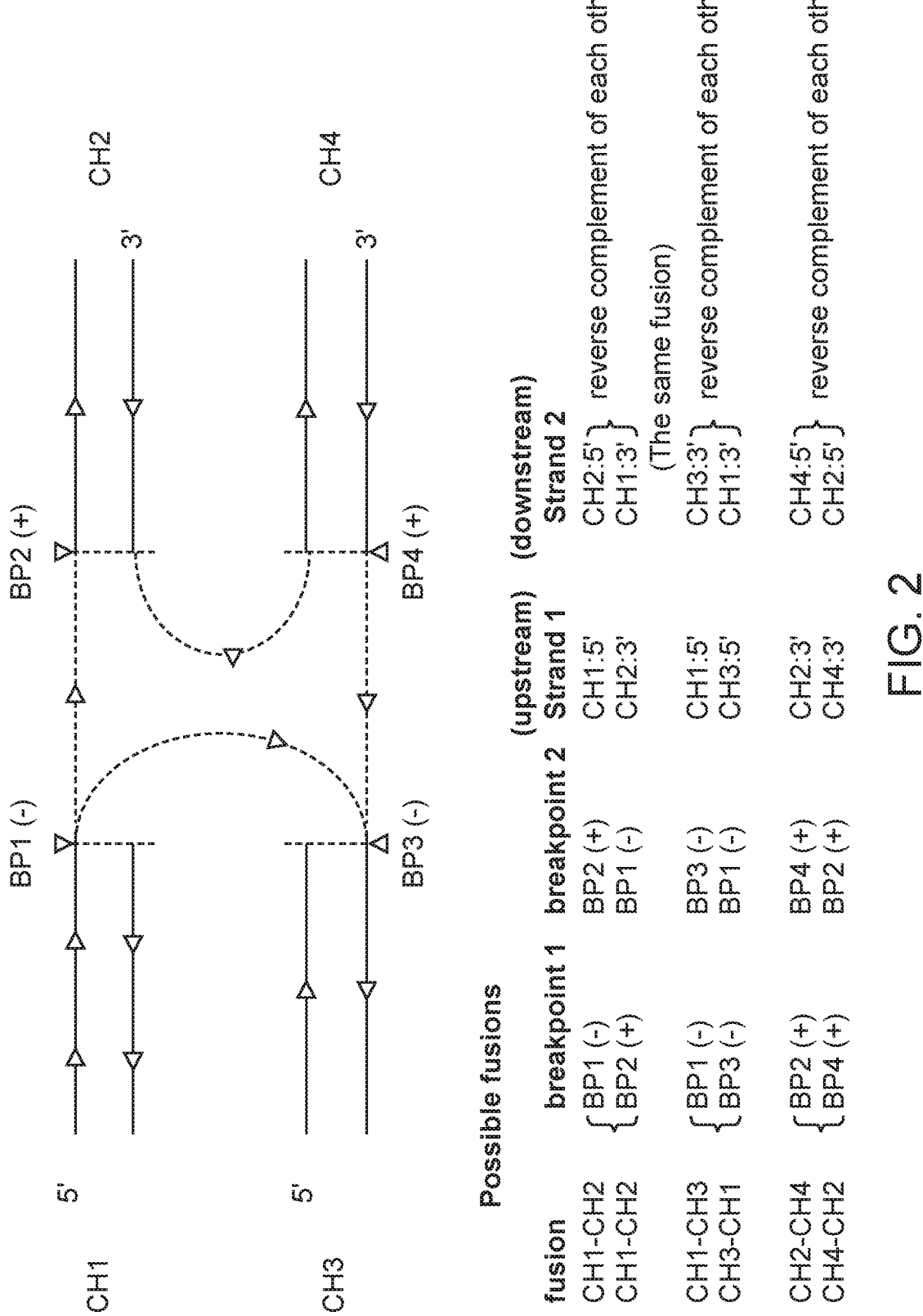
FIG. 2 depicts possible different scenarios to create a fused chromosome from two other chromosomes.
Figure 3A:
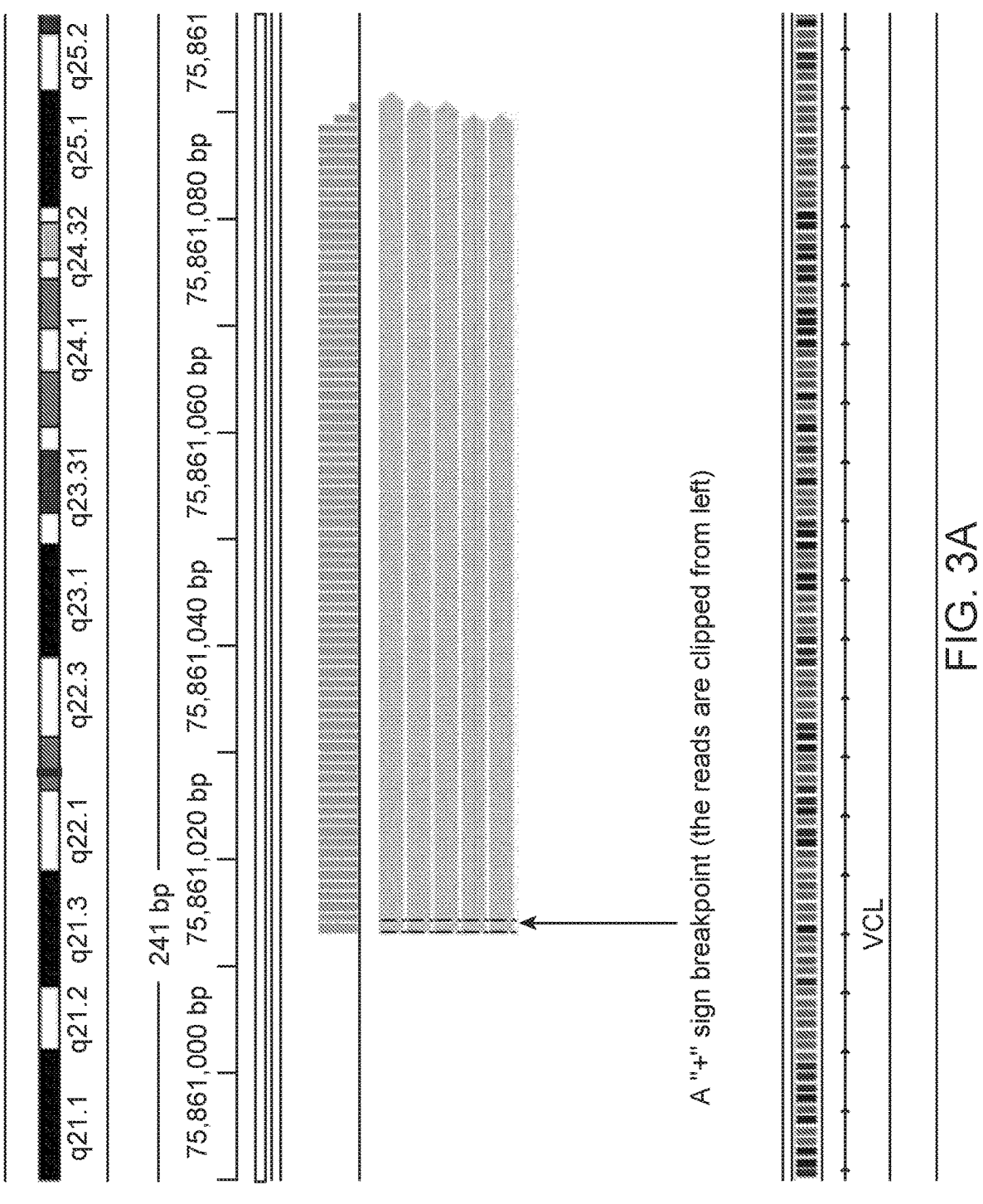
FIG. 3A shows an exemplary +/−breakpoint with read portions that are clipped from left/right, respectively.
Figure 3B:
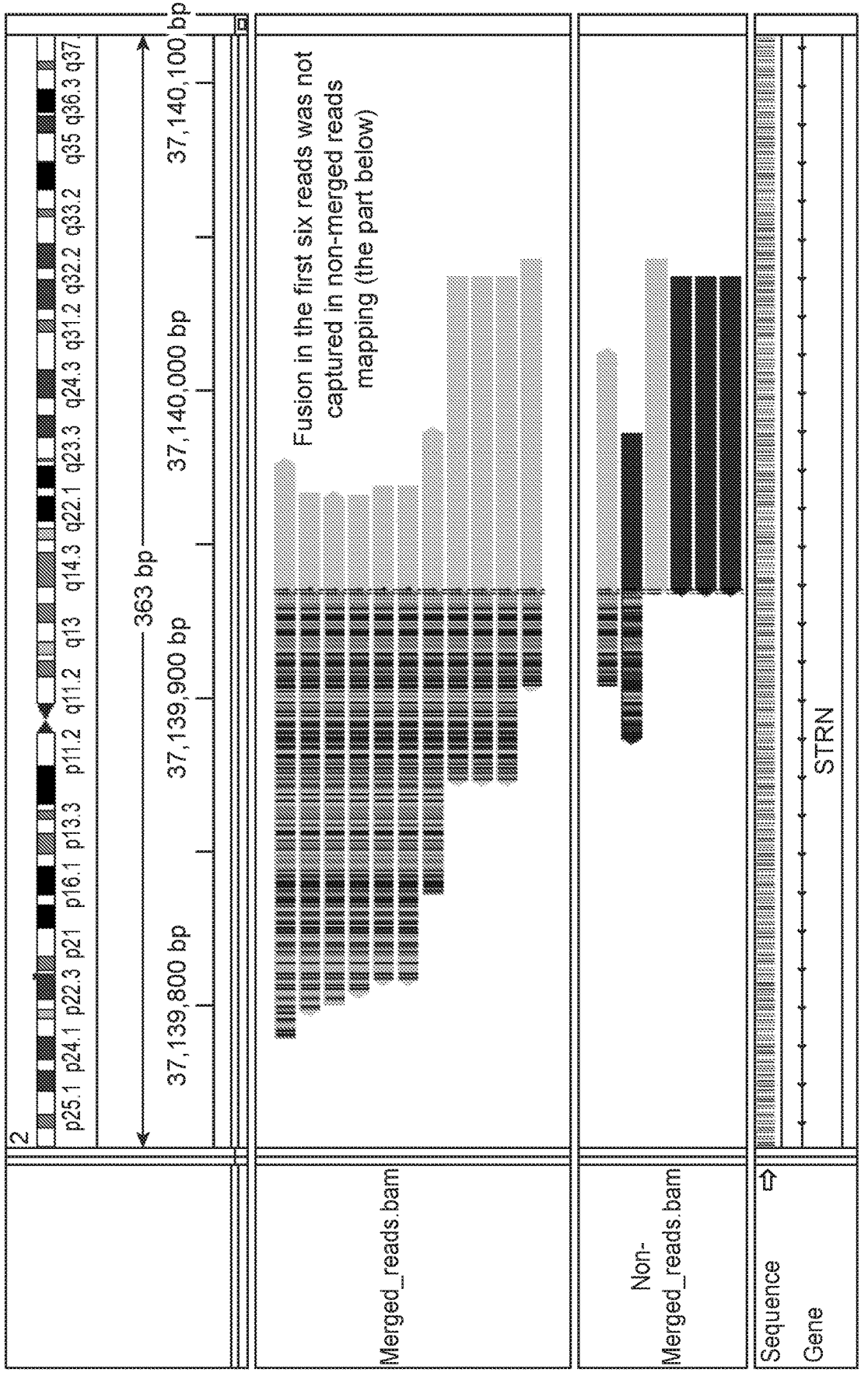
FIG. 3B shows exemplary merging process used with gene fusion detection.

The present invention relates to systems and methods for detecting gene fusions.

Precise mapping of the breakpoint of a fusion gene is challenging. Errors in sequencing and difficulty aligning a fusion gene are just two of the difficulties encountered when trying to map a breakpoint. The systems and methods described herein may provide one or more of the following advantages. The system can identify fusion genes that can contribute to tumor formation because fusion genes can produce much more active abnormal protein than non-fusion genes. The system accurately determines cancer presence, as fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulate the prostate cancer. Most fusion genes are found from hematological cancers, sarcomas, and prostate cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through event. Analysis of these gene fusions from a perspective of genome sequence and structure could provide relevant data to guide development of improved cancer diagnostics and targeted therapies.

FIG. 1 shows an exemplary process for determining gene fusion. In general, the process captures genetic data from sequencer and applies merging techniques that align and connect the sequenced Pair-End reads of which the insert size is smaller than the sum of the two read length and after merging assigns a unique read identifier (read ID) to each read (12). Next, the process extracts all breakpoints and locates fusion candidates (16). The process then forms fusion sets based on breakpoint pairs and determines statistics for fusion clusters (20). Fusion clusters are then identified by matching predetermined criteria as detected fusions (24).

Details on the process of FIG. 1 are discussed next. Cancerous cells may have chromosomes that are fused together. If such a chromosome is sequenced, it will generate reads that can be mapped into two different zones (on the same or different chromosomes) of the genome. This behavior is utilized to detect fusion.

Before mapping, a unique read identifier (read ID) is assigned to each read and would be encoded in the read header in one or more FASTQ file(s), as detailed below. Alternatively, a unique molecule, such as an oligonucleotide comprising a unique barcode, can be used instead of the read ID. Once the FASTQ file(s) is (are) mapped, this encoded read ID will be retrieved and it can easily show what hits are coming from the same original read. Next, the process extracts all the breakpoints: a fused read (a read contains the sequencing data of a partial DNA molecule coming from a fused chromosome) cannot be mapped as a whole to the genome and the mapper maps different portions of them to different locations on the genome. This presents a challenge when using conventional techniques to attempt breakpoint mapping. Each mapped portion of such reads is clipped from one or both sides. A breakpoint is a point on the genome where at least one mapped portion of a fused read is clipped. Breakpoints are independent of the reads in their identity and are identified by their sign, chromosome and position. A +/−breakpoint has read portions that are clipped from left/right, respectively. All the reads that are clipped or split from the same side in a position are listed in the related breakpoint read list. Breakpoints also can keep other statistics, like number of reads and molecules that are clipped or split at the breakpoint; or the number of wild-type reads and molecules that pass over the breakpoint. The gene information at the breakpoint position also can be provided. By assigning breakpoints, with or without clustering, the methods and systems described herein can be used to accurately determine the locus where gene fusion has occurred.

The process then finds fusions: every two mapped read portions with common read IDs that belong to two breakpoints with appropriate signs is a potential fusion candidate. They also need to have the correct piece order (their location in original read before mapping), that shows the read portion were originally located next to each other, to be considered a true fusion candidate. In addition, the resulting fusion must be biologically possible in terms of sequence strands. This simply means that if the read portions are mapped on the same strand (both 5' strand or both 3' strand) then the breakpoints' signs must disagree and vice versa. An example of this is shown in FIG. 2.

All extracted fusion candidates are put in fusion sets based on the breakpoint pairs. Fusion sets also can keep statistics like breakpoint IDs and number of molecules and reads that are contained in the set. These statistics may be tracked.

Clustering is then performed. All fusion sets with close enough breakpoints will be grouped in a fusion cluster. As a result, a fusion cluster is defined between two regions in in the genome. The present disclosure also provides determining for a fusion cluster a number of fused molecules for each partner, the number of fused reads for each partner, a number of wild-type molecules for each partner, a number of wild-type reads or molecules for each partner, or a fusion percentage for each partner as a ratio of fused molecules over total molecule for each partner.

Figure 5:
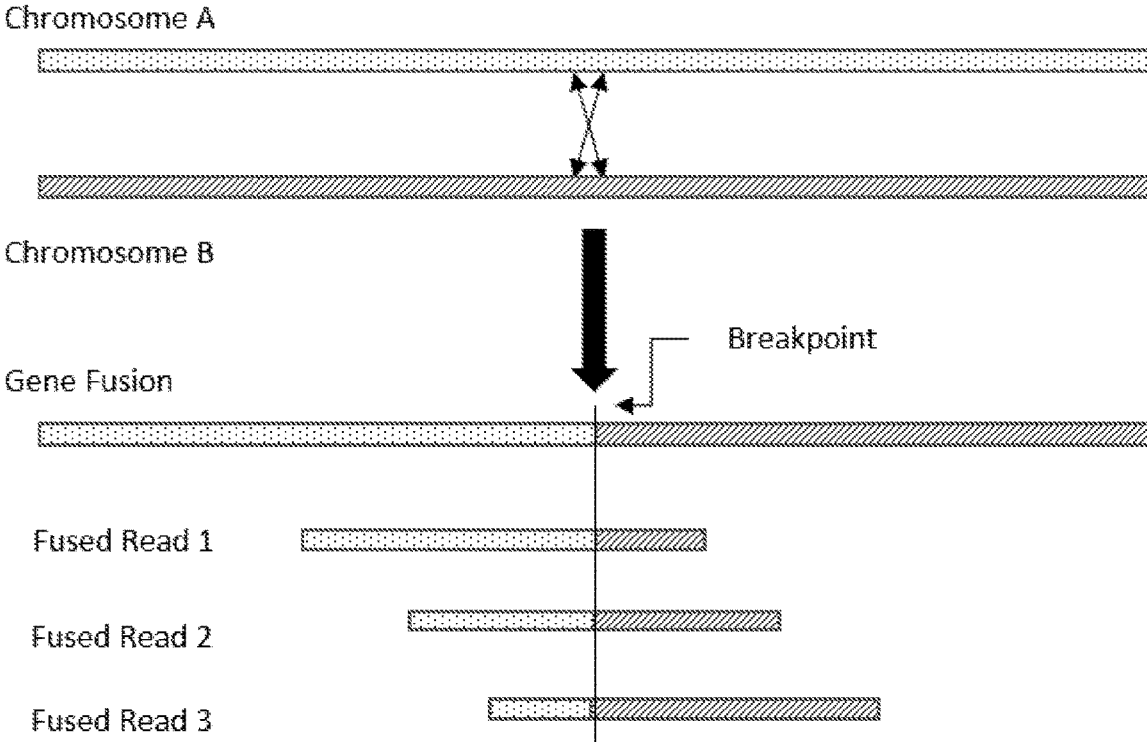
FIG. 5 shows an exemplary gene fusion between Chromosome A and Chromosome B, and DNA fused reads mapping across the breakpoint.

FIG. 5 shows a hypothetical gene fusion between Chromosome A and Chromosome B. As a result of crossing over, the gene fusion contains a portion of each chromosome. The point of cross over is referred to as the breakpoint. In cell free DNA, DNA fragments may map across the breakpoint, such as Fused Read 1, Fused Read 2 and Fused Read 3.

Figure 6:
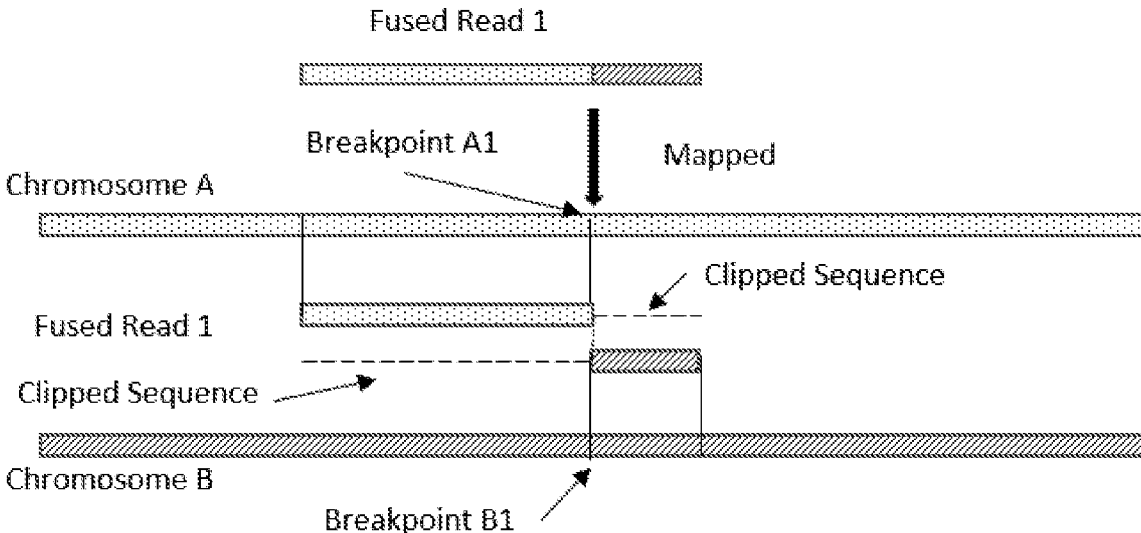
FIG. 6 shows the exemplary mapping of a DNA fragment to two locations in a reference genome.

Sequencing produces sequences of the DNA fragments. Software marks each sequence with an identifying tag. Software also maps these resultant sequences onto a reference genome. FIG. 6 shows hypothetical mapping of Fused Read 1 to a reference genome. Mapping software will map a sequence of a fused read to wherever in the reference genome sufficient homology is found. Ambiguous sequences can be mapped to multiple locations in the reference genome.

In the case of a fused read that maps across a breakpoint of a fusion gene, the software typically will map the sequence of a fused read twice, once to each chromosome. However, in each case, the mapping software cannot properly map a portion of the sequence (a subsequence) to the reference genome. Accordingly, the mapped sequence will include both a sub-sequence that maps to the reference genome and a sub-sequence that, as a result of poor homology, does not map to the same locus. Such a sub-sequence is referred to as a "clipped" sequence. The point on the reference genome at which the read is clipped is the breakpoint.

Because each sequence bears an identifying tag, a sequence mapped to two different locations can be identified as originating from the same original sequence due to identical tags. So, for example, a sub-sequence of the sequence having sufficient homology is mapped to Chromosome A and a sub-sequence of the sequence having insufficient homologogy is clipped. Similarly, the mapping software will map the sequence to Chromosome B, clipping the sequence where there is insufficient homology.

However, as a result of several factors, including errors in sequencing and characteristics of the mapping algorithm, a DNA fragment including a breakpoint of a fusion gene may not map precisely to the breakpoint locus on each of the reference chromosomes. For example, the mapping software may identify the breakpoint of a sequence somewhat upstream or somewhat downstream of the actual breakpoint.

Because each sequence bears an identifying tag, a sequence mapped to two different locations can be identified as originating from the same original sequence due to identical tags. So, for example, a sub-sequence of the sequence having sufficient homology is mapped to Chromosome A and a sub-sequence of the sequence having insufficient homologogy is clipped. Similarly, the mapping software will map the sequence to Chromosome B, clipping the sequence where there is insufficient homology.

Figure 7:
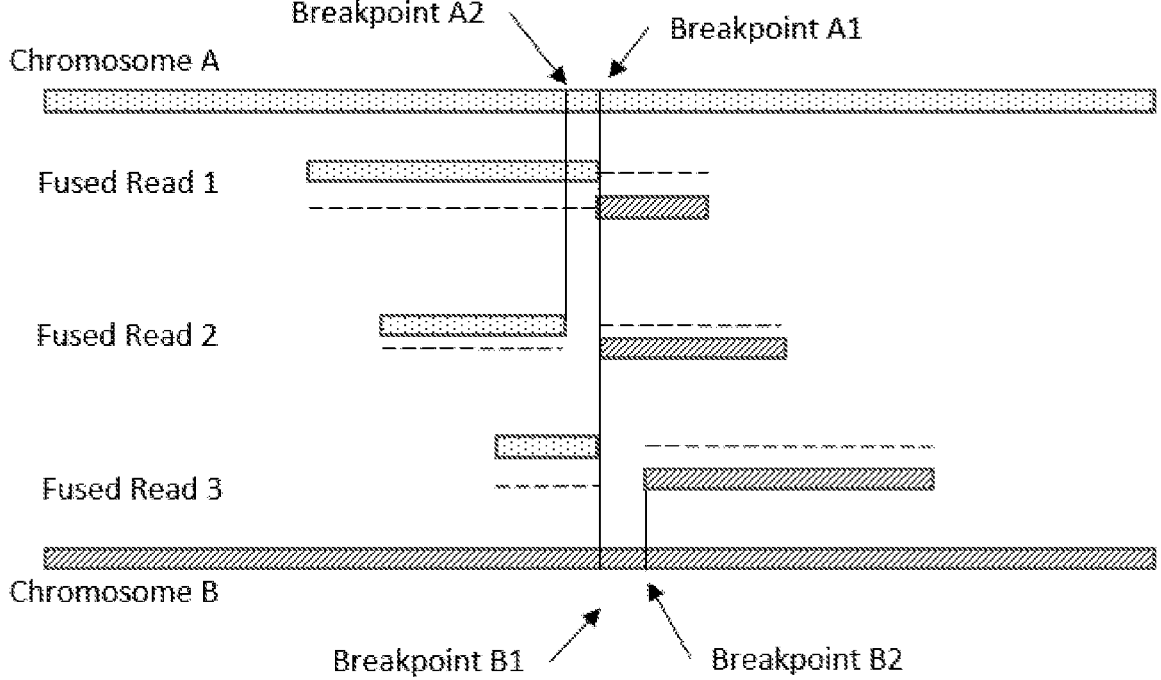
FIG. 7 shows exemplary fused reads in which mapped breakpoints are differently located.

However, as a result of several factors, including errors in sequencing and characteristics of the mapping algorithm, a DNA fragment including a breakpoint of a fusion gene may not map precisely to the breakpoint locus on each of the reference chromosomes. For example, the mapping software may identify the breakpoint of a sequence somewhat upstream or somewhat downstream of the actual breakpoint. These errors can affect the accuracy of, for example, a cancer diagnosis that depends upon accurate gene fusion information. The present disclosure Several hypothetical mapping errors are shown in FIG. 7. Fused Read 1 maps properly, with breakpoints indicated in the reference chromosomes as Breakpoint A1 and Breakpoint B1 (first and second breakpoints). This fused read has breakpoint pair A1-B1. Fused Read 2 maps improperly, with the breakpoint for Chromosome 1 determined to be upstream, at Breakpoint A2 (first breakpoint). However, the breakpoint in Chromosome B is mapped correctly at Breakpoint B1 (second breakpoint). This fused read has breakpoint pair A2-B1. Fused Read 3 also maps improperly, with the breakpoint for Chromosome A mapped correctly at Breakpoint A1 (first breakpoint), but the breakpoint for Chromosome B determined to be downstream, at Breakpoint B2 second breakpoint). This fused read has breakpoint pair A1-B2. In such a situation, software has identified several breakpoints for the fusion gene.

According to a method of this disclosure, in order to call a breakpoint in a fusion gene, mapped sequences are grouped into sets based on common breakpoint pairs and then into clusters based on breakpoints within a predetermined base distance in the reference genome.

Figure 8:
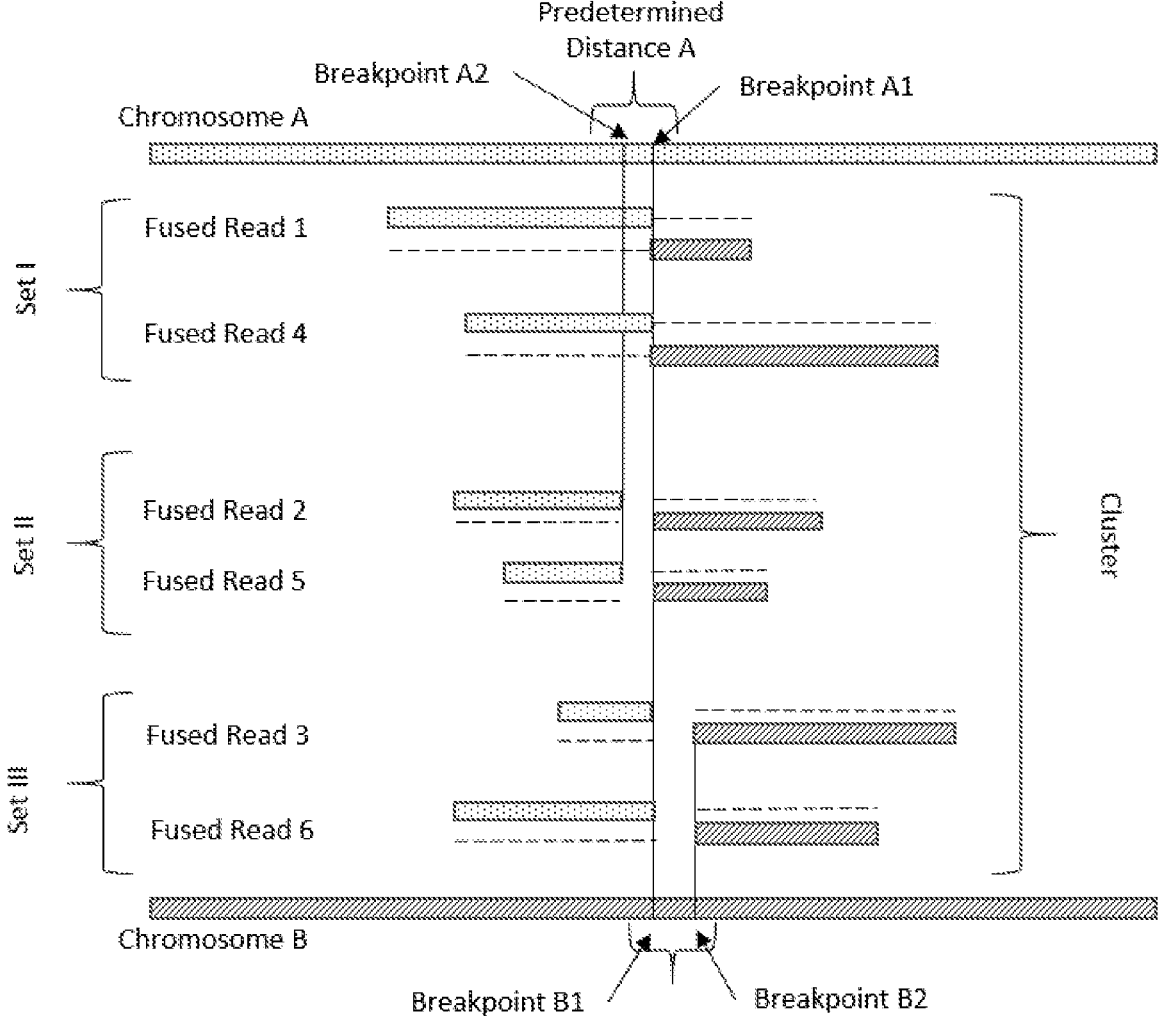
FIG. 8 shows exemplary grouping of mapped fused reads into sets and sets into clusters for calling a fusion gene breakpoint.

Such a method is described in FIG. 8. Sequences for Fused Reads 1, 2, 3, 4, 5 and 6 are mapped to Chromosomes A and B of the reference genome. Sequences in which the breakpoints on both sides of the fusion are grouped into a set. In the example, Fused Reads 1 and 4 share breakpoint pair A1 and B1, and are grouped into Set I. Fused Reads 2 and 5 share breakpoint pair A2 and B1, and are grouped into Set II. Fused Reads 3 and 6 share breakpoint pair A1 and B2, and are grouped into Set III.

In this example, breakpoints A1 and A2 are within a predetermined genetic distance A (e.g., 10 bases), and breakpoints B1 and B2 are within a predetermined genetic distance B. Accordingly, Sets I, II and III and grouped into a cluster.

The fusion gene breakpoint is called using selection criteria selected by the user. In some embodiments, the criteria comprise having more than one molecule in the cluster and/or having at least a molecule with both Watson and Crick strands. In one method, the breakpoint in each chromosome is determined by a voting method, in which the breakpoint among all the breakpoints having the most associated fused reads is called as the fusion gene breakpoint. In other methods, breakpoints of different sequences may be weighted using a quality algorithm. In the example of FIG. 8, in Chromosome A, Breakpoint A1 is associated with four fused reads, while Breakpoint A2 is associated with two fused reads. Therefore, the first gene fusion breakpoint is called at A1. In Chromosome B, Breakpoint B1 is associated with four fused reads, while Breakpoint B2 is associated with two fused reads. Therefore, the second gene fusion breakpoint is called at B1.

Figure 9A:
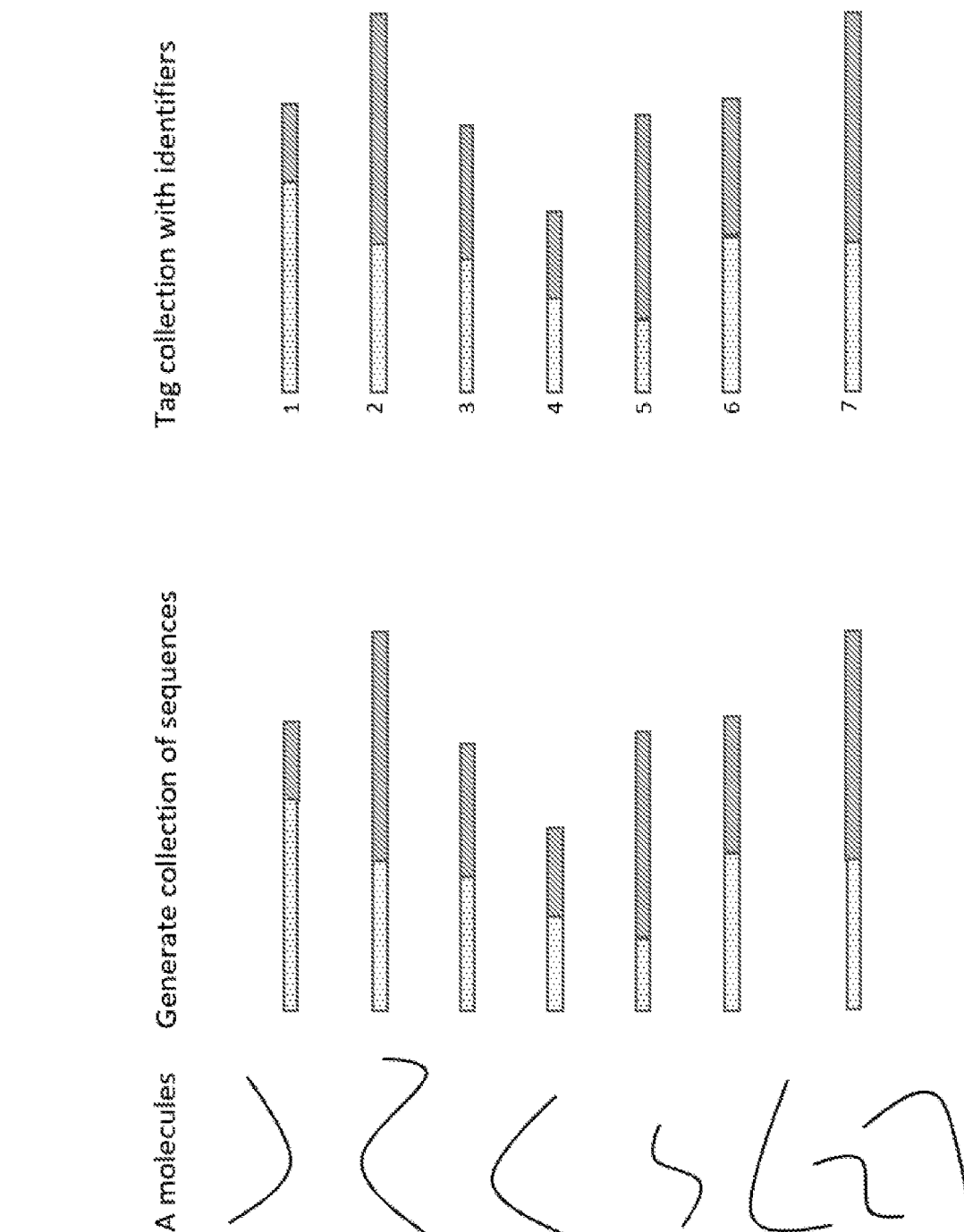
Figure 9B:
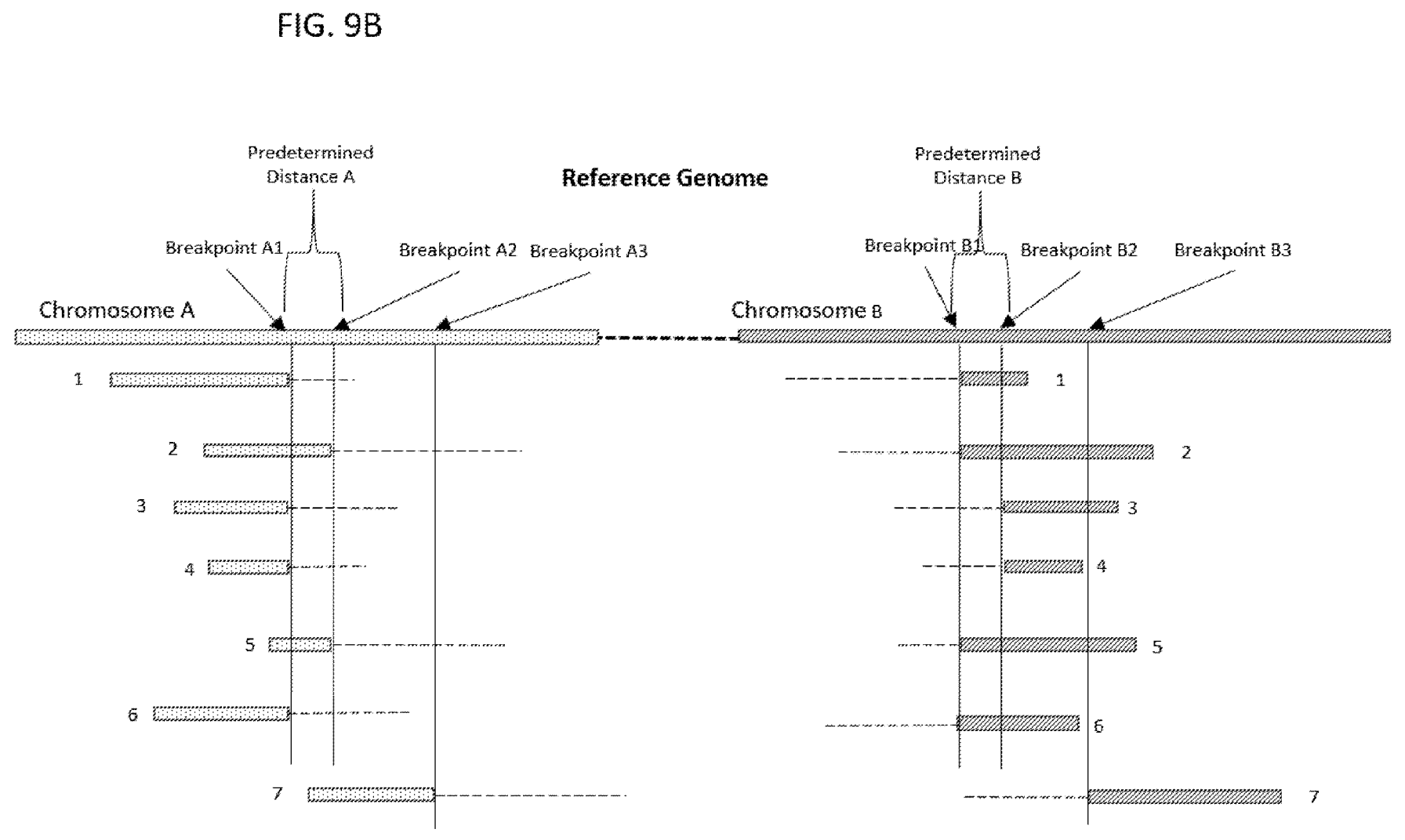

Another exemplary method is shown in FIGS. 9A-9C. DNA molecules are sequenced using a DNA sequencing system, such as a high throughput sequencer. Sequences can be analyzed to generate consensus sequences of original molecules in the collection. The collection of sequences generated are tagged with unique identifiers (in this case, 1-7). The sequences are mapped to a reference genome. In this example, the sequences each map to two different locations in the reference genome. Mapped portions are depicted as bars, while clipped portions are depicted as dashed lines. Breakpoints of all the sequences are identified. In this example, the breakpoints on chromosome A are A1, A2 and A3. The breakpoints on chromosome B are B1, B2 and B3. Mapped reads are organized into sets based on common breakpoints. Breakpoint pairs are determined as pairs of sequences having the same identifier and the same breakpoints on each chromosome. A predetermined distance on the chromosome to cluster breakpoints is determined. In this example, the cluster includes breakpoints A1 and A2, and B1 and B2. Breakpoints A3 and B3 are outside of the predetermined distance and, therefore, are not included in the cluster. A breakpoint pair in the original molecules is called based on selected criteria. In this example, the criteria are based on voting. Accordingly, breakpoints A1 and B1 are called as the breakpoint pair based on having a majority of the molecules within the cluster.

The system can handle multiple alignments of short sequences that is commonly seen in splicing. Longer sequences can be obtained around the fusion point to confirm their alignments. To reduce the false-positive rate, a list of filters, including read number, sequence similarity, read position distribution filter can be used to provide results with high specificity. In addition, expression estimation tool RSEM (RNA-Seq by Expectation Maximization) can be used to apply the Expectation Maximization (EM) algorithm with sparse optimization to estimate chimerical transcript abundance. Furthermore, this abundance quantification can be increase the identification accuracy. Taken together, these features allow the system to provide a more complete view of gene fusion events.

The system can encompass obtaining a plurality of sequence reads from one or more samples in any suitable file format, identifying sets of duplicative sequence reads, and storing only one read for each set of the duplicative sequence reads. Suitable file formats include the FASTA and FASTQ file formats. FASTA and FASTQ are common file formats used to store raw sequence reads from high throughput sequencing. FASTQ files store an identifier for each sequence read, the sequence, and the quality score string of each read. FASTA files store the identifier and sequence only. These two file formats are the inputs to many common sequencing alignment and assembly algorithms. The invention recognizes that the read sequence information for FASTQ and FASTA files within and across samples tends to be highly redundant or duplicative. This means that many of the sequence reads will consist of the same sequence. Methods of the invention exploit this redundancy to achieve a many-fold reduction in file size, and there is no loss in the retrieval of the stored data. For example, the invention can be used to read the FASTA/FASTQ file associated with a sample and store only the unique read sequences in a master read sequence file.

The system further encompasses collecting meta information, such as a read identifier, for each read that has the same sequence as the identified unique sequence. This meta information can then be written to a file for that sample in which the meta information is correlated to the unique sequence reads identified in original FASTA/FASTQ file and now stored in a master read sequence file. Because this new file does not contain the duplicative information found in the original file, it is smaller and easier to transfer than the original file. Moreover, the compressed file need not contain any actual sequence data at all. In certain aspects, the compressed file may simply contain the identifier for the sequence read indexed to the unique sequences stored in the master file.

Sequence data can be compressed by obtaining—using a computer system comprising a processor coupled to a non-transitory memory—a plurality of sequence reads. Each sequence read can include a sequence string as well as meta information. The sequence reads may be provided in the format of one or more FASTA or FASTQ files, for example, with the meta information including the description line (preceded by the ">" character) and optionally, in the case of FASTQ, quality scores. The sequence string preferably represents nucleotide sequence data, e.g., using IUPAC nucleotide codes. A subset of the sequence strings that contains only unique entries is identified. Systems and methods of the invention may then be used to write output that includes the identified subset and—for each of the plurality of sequence reads—the meta information for that sequence read with an indicator of the unique entry in the subset that represents that sequence read.

In some embodiments, the subset (i.e., containing only unique sequence reads) is written to a master reads file, which may be a text file. Preferably, the unique sequence reads are represented in the master reads file using IUPAC nucleotide codes so that the files are human-readable and further processing (e.g., using a scripting language such as Perl or Python) can be easily performed. The meta information may be written to compressed output files corresponding to the input FASTA or FASTQ files.

Methods can include reconstituting the original input from only the output and in certain embodiments the retrieval is lossless, even perfectly lossless. That is, the output may be processed to create new FASTA or FASTQ files comprising the plurality of sequence reads. Where the retrieval is lossless, the new FASTA or FASTQ files contain the same information as the FASTA or FASTQ files.

The invention is amenable with any suitable type of data file. In addition to the aforementioned FASTA and FASTQ files, sequence reads can also be captured in Variant Call Format (VCF) files. With advances in high throughput sequencing, it is common for multiple sequencing centers to detect variants in the human genome and report them through these VCF files. The invention can facilitate the development of a unified database to store variant information in VCF files from different sources in a way that allows researchers to perform complex allele-, sample-, and population-level queries across centers. The unified database can consolidate variant information in the VCF files from different samples by storing every unique allele (e.g. unique sequence read) on one universal allele table and by storing references of these unique alleles to associated samples and sample-level meta-data.

Implementations of the system can include a method for compressing sequence data. The method includes: obtaining—using a computer system comprising a processor coupled to a non-transitory memory—a plurality of sequence reads, each sequence read comprising a sequence string and meta information; identifying a subset of the sequence strings that contains only unique entries; writing output comprising the subset and—for each of the plurality of sequence reads—the meta information for that sequence read with an indicator of the unique entry in the subset that represents that sequence read. Preferably the output comprises one or more text files that store the subset using IUPAC nucleotide codes. Preferably, the output is stored as plain text (e.g., and may be opened using a text editor program and read on-screen by a person). In a preferred embodiment, the sequence read data is stored without loss. The method may include processing the output to create new FASTA or FASTQ files comprising the plurality of sequence reads. The plurality of sequence reads may be obtained as FASTA or FASTQ files and the new FASTA or FASTQ files may contain the same information as the FASTA or FASTQ files. In some embodiments, the output occupies less than % of the disk space required to store the obtained plurality of sequence reads.

General methods for obtaining samples, generating sequencing reads, and various types of sequencing useful for practicing the invention will now be described. It is to be understood that these exemplary methods are not limiting and may be modified as necessary by those skilled in the art.

Obtaining a plurality of sequence reads can include sequencing a nucleic acid from a sample to generate the sequence reads. As explained in detail below, obtaining a plurality of sequence reads can also include receiving sequencing data from a sequencer. Nucleic acid in a sample can be any nucleic acid, including for example, genomic DNA in a tissue sample, cDNA amplified from a particular target in a laboratory sample, or mixed DNA from multiple organisms. In some embodiments, the sample includes homozygous DNA from a haploid or diploid organism. For example, a sample can include genomic DNA from a patient who is homozygous for a rare recessive allele. In other embodiments, the sample includes heterozygous genetic material from a diploid or polyploidy organism with a somatic mutation such that two related nucleic acids are present in allele frequencies other than 50 or 100%, i.e., 20%, 5%, 1%, 0.1%, or any other allele frequency.

In one embodiment, nucleic acid template molecules (e.g., DNA or RNA) are isolated from a biological sample containing a variety of other components, such as proteins, lipids, and non-template nucleic acids. Nucleic acid template molecules can be obtained from any cellular material, obtained from animal, plant, bacterium, fungus, or any other cellular organism. Biological samples for use in the present invention also include viral particles or preparations. Nucleic acid template molecules can be obtained directly from an organism or from a biological sample obtained from an organism, e.g., from blood, serum, plasma, urine, cerebrospinal fluid, saliva, stool, lymph fluid, synovial fluid, cystic fluid, ascites, pleural effusion, amniotic fluid, chorionic villus sample, fluid from a preimplantation embryo, a placental sample, lavage and cervical vaginal fluid, interstitial fluid, a buccal swab sample, sputum, bronchial lavage, a Pap smear sample, or ocular fluid. Any tissue or body fluid specimen (e.g., a human tissue of bodily fluid specimen) may be used as a source for nucleic acid to use in the invention. Nucleic acid template molecules can also be isolated from cultured cells, such as a primary cell culture or cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin.

Nucleic acid obtained from biological samples may be fragmented to produce suitable fragments for analysis. Template nucleic acids may be fragmented or sheared to a desired length, using a variety of mechanical, chemical, and/or enzymatic methods. DNA may be randomly sheared via sonication using, for example, an ultrasonicator sold by Covaris (Woburn, Mass.), brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid is fragmented by sonication. In another embodiment, nucleic acid is fragmented by a hydroshear instrument. Generally, individual nucleic acid template molecules can be from about 2 kb bases to about 40 kb. In a particular embodiment, nucleic acids are about 6 kb-10 kb fragments. Nucleic acid molecules may be single-stranded, double-stranded, or double stranded with single-stranded regions (for example, stem- and loop-structures).

A biological sample may be lysed, homogenized, or fractionated in the presence of a detergent or surfactant as needed. Suitable detergents may include an ionic detergent (e.g., sodium dodecyl sulfate or N-lauroylsarcosine) or a nonionic detergent. Once a nucleic acid is extracted or isolated from the sample it may be amplified.

Amplification refers to production of additional copies of a nucleic acid sequence and is generally carried out using polymerase chain reaction (PCR) or other technologies known in the art. The amplification reaction may be any amplification reaction known in the art that amplifies nucleic acid molecules such as PCR. Other amplification reactions include nested PCR, PCR-single strand conformation polymorphism, ligase chain reaction, strand displacement amplification and restriction fragments length polymorphism, transcription based amplification system, rolling circle amplification, and hyper-branched rolling circle amplification, quantitative PCR, quantitative fluorescent PCR (QF-PCR), multiplex fluorescent PCR (MF-PCR), real time PCR (RTPCR), restriction fragment length polymorphism PCR (PCR-RFLP), in situ rolling circle amplification (RCA), bridge PCR, picotiter PCR, emulsion PCR, transcription amplification, self-sustained sequence replication, consensus sequence primed PCR, arbitrarily primed PCR, degenerate oligonucleotide-primed PCR, and nucleic acid based sequence amplification (NABSA). Amplification methods that can be used include those described in U.S. Pat. Nos. 5,242,794; 5,494,810; 4,988,617; and 6,582,938. In certain embodiments, the amplification reaction is PCR as described, for example, U.S. Pat. No. 4,683,195; and U.S. Pat. No. 4,683,202, hereby incorporated by reference. Primers for PCR, sequencing, and other methods can be prepared by cloning, direct chemical synthesis, and other methods known in the art. Primers can also be obtained from commercial sources such as Eurofins MWG Operon (Huntsville, Ala.) or Life Technologies (Carlsbad, Calif.).

Amplification adapters may be attached to the fragmented nucleic acid. Adapters may be commercially obtained, such as from Integrated DNA Technologies (Coralville, Iowa). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase, available commercially from New England Biolabs (Ipswich, Mass.). Methods for using ligases are well known in the art. The polymerase may be any enzyme capable of adding nucleotides to the 3' and the 5' terminus of template nucleic acid molecules.

The ligation may be blunt ended or utilize complementary overhanging ends. In certain embodiments, the ends of the fragments may be repaired, trimmed (e.g. using an exonuclease), or filled (e.g., using a polymerase and dNTPs) following fragmentation to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A is used to guide ligation of fragments with a single T overhanging from the 5'-end in a method referred to as T-A cloning. Alternatively, because the possible combinations of overhangs left by the restriction enzymes are known after a restriction digestion, the ends may be left as-is, i.e., ragged ends. In certain embodiments, double stranded oligonucleotides with complementary overhanging ends are used.

Embodiments of the invention involve attaching the barcode sequences to the template nucleic acids. In certain embodiments, a barcode is attached to each fragment. In other embodiments, a plurality of barcodes, e.g., two barcodes, are attached to each fragment. A barcode sequence generally includes certain features that make the sequence useful in sequencing reactions. For example the barcode sequences are designed to have minimal or no homopolymer regions, i.e., 2 or more of the same base in a row such as AA or CCC, within the barcode sequence. The barcode sequences are also designed so that they are at least one edit distance away from the base addition order when performing base-by-base sequencing, ensuring that the first and last base do not match the expected bases of the sequence.

The barcode sequences are designed such that each sequence is correlated to a particular portion of nucleic acid, allowing sequence reads to be correlated back to the portion from which they came. In certain embodiments, the barcode sequences range from about 5 nucleotides to about 15 nucleotides. In a particular embodiment, the barcode sequences range from about 4 nucleotides to about 7 nucleotides. Since the barcode sequence is sequenced along with the template nucleic acid, the oligonucleotide length should be of minimal length so as to permit the longest read from the template nucleic acid attached. For example, a plurality of DNA barcodes can comprise various numbers of sequences of nucleotides. In certain embodiments, the barcode sequences comprise 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. When attached to only one end of a polynucleotide, the plurality of DNA barcodes can produce 2, 3, 4, 5, 6, 7, 8, 9, 10, 11, 12, 13, 14, 15, 16, 17, 18, 19, 20, 21, 22, 23, 24, 25, 26, 27, 28, 29, 30 or more different identifiers. Alternatively, when attached to both ends of a polynucleotide, the plurality DNA barcodes can produce 4, 9, 16, 25, 36, 49, 64, 81, 100, 121, 144, 169, 196, 225, 256, 289, 324, 361, 400 or more different identifiers (which is the ^2 of when the DNA barcode is attached to only 1 end of a polynucleotide).

Generally, the barcode sequences are spaced from the template nucleic acid molecule by at least one base (minimizes homo-polymeric combinations). In certain embodiments, the barcode sequences are attached to the template nucleic acid molecule, e.g., with an enzyme. The enzyme may be a ligase or a polymerase, as discussed below.

Amplification or sequencing adapters or barcodes, or a combination thereof, may be attached to the fragmented nucleic acid. Such molecules may be commercially obtained, such as from Integrated DNA Technologies (Coralville, Iowa). In certain embodiments, such sequences are attached to the template nucleic acid molecule with an enzyme such as a ligase. Suitable ligases include T4 DNA ligase and T4 RNA ligase, available commercially from New England Biolabs (Ipswich, Mass.). The ligation may be blunt ended or via use of complementary overhanging ends. In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A can guide ligation of fragments with a single T overhanging from the 5'-end in a method referred to as T-A cloning. Alternatively, because the possible combinations of overhangs left by the restriction enzymes are known after a restriction digestion, the ends may be left as-is, i.e., ragged ends. In certain embodiments double stranded oligonucleotides with complementary overhanging ends are used.

After any processing steps (e.g., obtaining, isolating, fragmenting, amplification, or barcoding), nucleic acid can be sequenced.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, SOLiD sequencing targeted sequencing, single molecule real-time sequencing, exon sequencing, electron microscopy-based sequencing, panel sequencing, transistor-mediated sequencing, direct sequencing, random shotgun sequencing, whole-genome sequencing, sequencing by hybridization, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, real-time sequencing, reverse-terminator sequencing, nanopore sequencing, MS-PET sequencing, and a combination thereof. In some embodiments, the sequencing method is massively parallel sequencing, that is, simultaneously (or in rapid succession) sequencing any of at least 100, 1000, 10,000, 100,000, 1 million, 10 million, 100 million, or 1 billion polynucleotide molecules. In some embodiments, sequencing can be performed by a gene analyzer such as, for example, gene analyzers commercially available from Illumina or Applied Biosystems. Sequencing of separated molecules has more recently been demonstrated by sequential or single extension reactions using polymerases or ligases as well as by single or sequential differential hybridizations with libraries of probes. Sequencing may be performed by a DNA sequencer (e.g., a machine designed to perform sequencing reactions).

A sequencing technique that can be used includes, for example, use of sequencing-by-synthesis systems. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is removed and the process is then repeated.

Another example of a DNA sequencing technique that can be used is ion semiconductor sequencing using, for example, a system sold under the trademark ION TORRENT by Ion Torrent by Life Technologies (South San Francisco, Calif). Ion semiconductor sequencing is described, for example, in Rothberg, et al., An integrated semiconductor device enabling non-optical genome sequencing, Nature 475:348-352 (2011); U.S. Pub. 2010/0304982; U.S. Pub. 2010/0301398; U.S. Pub. 2010/0300895; U.S. Pub. 2010/0300559; and U.S. Pub. 2009/0026082, the contents of each of which are incorporated by reference in their entirety.

Another example of a sequencing technology that can be used is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. No. 7,960,120; U.S. Pat. No. 7,835,871; U.S. Pat. No. 7,232,656; U.S. Pat. No. 7,598,035; U.S. Pat. No. 6,911,345; U.S. Pat. No. 6,833,246; U.S. Pat. No. 6,828,100; U.S. Pat. No. 6,306,597; U.S. Pat. No. 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Another example of a sequencing technology that can be used includes the single molecule, real-time (SMRT) technology of Pacific Biosciences (Menlo Park, Calif). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used is nanopore sequencing (Soni & Meller, 2007, Progress toward ultrafast DNA sequence using solid-state nanopores, Clin Chem 53(11):1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope as described, for example, by Moudrianakis, E. N. and Beer M., in Base sequence determination in nucleic acids with the electron microscope, III. Chemistry and microscopy of guanine-labeled DNA, PNAS 53:564-71 (1965). In one example of the technique, individual DNA molecules are labeled using metallic labels that are distinguishable using an electron microscope. These molecules are then stretched on a flat surface and imaged using an electron microscope to measure sequences.

Sequencing according to embodiments of the invention generates a plurality of reads. Reads according to the invention generally include sequences of nucleotide data less than about 150 bases in length, or less than about 90 bases in length. In certain embodiments, reads are between about 80 and about 90 bases, e.g., about 85 bases in length. In some embodiments, methods of the invention are applied to very short reads, i.e., less than about 50 or about 30 bases in length. Sequence read data can include the sequence data as well as meta information. Sequence read data can be stored in any suitable file format including, for example, VCF files, FASTA files or FASTQ files, as are known to those of skill in the art.

FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There should be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer. Cock et al., 2009, The Sanger FASTQ file format for sequences with quality scores, and the Solexa/Illumina FASTQ variants, Nucleic Acids Res 38(6):1767-1771.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "-". In a preferred embodiment, the sequence data will use the A, T, C, G, and N characters, optionally including "-" or U as-needed (e.g., to represent gaps or uracil).

In some embodiments, the at least one master sequence read file and the output file are stored as plain text files (e.g., using encoding such as ASCII; ISO/IEC 646; EBCDIC; UTF-8; or UTF-16). A computer system provided by the invention may include a text editor program capable of opening the plain text files. A text editor program may refer to a computer program capable of presenting contents of a text file (such as a plain text file) on a computer screen, allowing a human to edit the text (e.g., using a monitor, keyboard, and mouse). Exemplary text editors include, without limit, Microsoft Word, emacs, pico, vi, BBEdit, and TextWrangler. Preferably, the text editor program is capable of displaying the plain text files on a computer screen, showing the meta information and the sequence reads in a human-readable format (e.g., not binary encoded but instead using alphanumeric characters as they would be used in print human writing).

While methods have been discussed with reference to FASTA or FASTQ files, methods and systems of the invention may be used to compress any suitable sequence file format including, for example, files in the Variant Call Format (VCF) format. A typical VCF file will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. The header section may be treated as the meta information to write to the compressed files and the data section may be treated as the lines, each of which will be stored in a master file only if unique.

Certain embodiments of the invention provide for the assembly of sequence reads. In assembly by alignment, for example, the reads are aligned to each other or to a reference. By aligning each read, in turn to a reference genome, all of the reads are positioned in relationship to each other to create the assembly. In addition, aligning or mapping the sequence read to a reference sequence can also be used to identify variant sequences within the sequence read. Identifying variant sequences can be used in combination with the methods and systems described herein to further aid in the diagnosis or prognosis of a disease or condition, or for guiding treatment decisions.

In some embodiments, any or all of the steps of the invention are automated. Alternatively, methods of the invention may be embodied wholly or partially in one or more dedicated programs, for example, each optionally written in a compiled language such as C++ then compiled and distributed as a binary. Methods of the invention may be implemented wholly or in part as modules within, or by invoking functionality within, existing sequence analysis platforms. In certain embodiments, methods of the invention include a number of steps that are all invoked automatically responsive to a single starting queue (e.g., one or a combination of triggering events sourced from human activity, another computer program, or a machine). Thus, the invention provides methods in which any or the steps or any combination of the steps can occur automatically responsive to a queue. Automatically generally means without intervening human input, influence, or interaction (i.e., responsive only to original or pre-queue human activity).

The system also encompasses various forms of output, which includes an accurate and sensitive interpretation of the subject nucleic acid. The output of retrieval can be provided in the format of a computer file. In certain embodiments, the output is a FASTA file, FASTQ file, or VCF file. Output may be processed to produce a text file, or an XML file containing sequence data such as a sequence of the nucleic acid aligned to a sequence of the reference genome. In other embodiments, processing yields output containing coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence.

A CIGAR string follows an established motif. Each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). For example, the CIGAR string 2MD3M2D2M will mean that the alignment contains 2 matches, 1 deletion (number 1 is omitted in order to save some space), 3 matches, 2 deletions and 2 matches.

As contemplated by the invention, the functions described above can be implemented using a system of the invention that includes software, hardware, firmware, hardwiring, or any combinations of these. Features implementing functions can also be physically located at various positions, including being distributed such that portions of functions are implemented at different physical locations.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Figure 4:
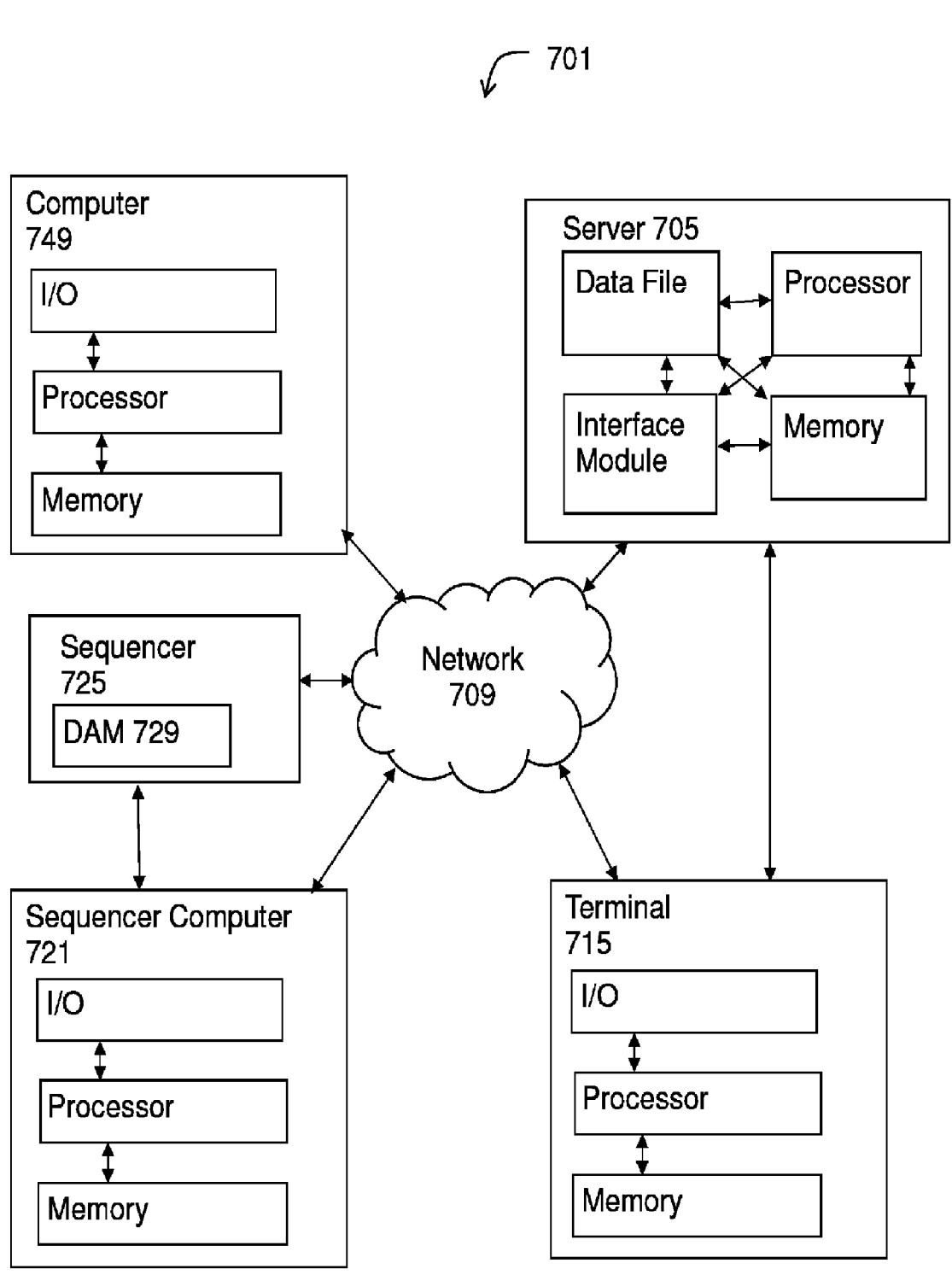
FIG. 4 diagrams a system of the invention.

FIG. 4 diagrams a system 701 suitable for performing methods of the invention. As shown in FIG. 7, system 701 may include one or more of a server computer 705, a terminal 715, a sequencer 715, a sequencer computer 721, a computer 749, or any combination thereof. Each such computer device may communicate via network 709. Sequencer 725 may optionally include or be operably coupled to its own, e.g., dedicated, sequencer computer 721 (including any input/output mechanisms (I/O), processor, and memory). Additionally or alternatively, sequencer 725 may be operably coupled to a server 705 or computer 749 (e.g., laptop, desktop, or tablet) via network 709. Computer 749 includes one or more processor, memory, and I/O. Where methods of the invention employ a client/server architecture, any steps of methods of the invention may be performed using server 705, which includes one or more of processor, memory, and I/O, capable of obtaining data, instructions, etc., or providing results via an interface module or providing results as a file. Server 705 may be engaged over network 709 through computer 749 or terminal 715, or server 705 may be directly connected to terminal 715. Terminal 515 is preferably a computer device. A computer according to the invention preferably includes one or more processor coupled to an I/O mechanism and memory.

A processor may be provided by one or more processors including, for example, one or more of a single core or multi-core processor. An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof. Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system 701, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

In some embodiments, the methods and systems of the present disclosure can be used to diagnose a disease or condition, e.g., cancer. The term "diagnosis" as used herein refers to methods by which the skilled worker can estimate and/or determine whether or not a patient is suffering from a given disease or condition. In some embodiments, the methods of the invention can be used in the prognosis of a disease of a disease or condition, e.g., cancer. The term "prognosis" as used herein refers to the likelihood of a disease or condition progression, including recurrence of a disease or condition. In some embodiments, the methods of the invention can be used to assess the risk of developing a disease or condition, e.g., cancer. For example, the methods and systems described herein can be used to identify a breakpoint or gene fusion associated with a particular diagnosis, prognosis, or risk of developing a disease or condition. Moreover, the methods and systems described herein can be used to identify a breakpoint or gene fusion associated with a predicted therapeutic outcome. Thus, the methods and systems can be used to guide the treatment of the disease or condition (e.g., by administering a compound or agent to a subject), or to guide the preparation of a medicament for treatment of the disease or condition.

As used herein, "treating" a disease or condition refers to taking steps to obtain beneficial or desired results, including clinical results. Beneficial or desired clinical results include, but are not limited to, alleviation or amelioration of one or more symptoms associated with diseases or conditions. As used herein, "administering" or "administration of" a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorbtion, e.g., through a skin duct). A compound or agent can also appropriately be introduced by rechargeable or biodegradable polymeric devices or other devices, e.g., patches and pumps, or formulations, which provide for the extended, slow, or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. In some embodiments, a compound or an agent is administered orally, e.g., to a subject by ingestion, or intravenously, e.g., to a subject by injection. In some embodiments, the orally administered compound or agent is in an extended release or slow release formulation, or administered using a device for such slow or extended release.

As used herein, the term "cancer" includes, but is not limited to, various types of malignant neoplasms, most of which can invade surrounding tissues, and may metastasize to different sites (see, for example, PDR Medical Dictionary, 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Such abnormal tissue shows partial or complete lack of structural organization and functional coordination with the normal tissue which may be either benign (such as a benign tumor) or malignant (such as a malignant tumor). Examples of general categories of cancer include, but are not limited to, carcinomas (malignant tumors derived from epithelial cells such as, for example, common forms of breast, prostate, lung and colon cancer), sarcomas (malignant tumors derived from connective tissue or mesenchymal cells), lymphomas (malignancies derived from hematopoietic cells), leukemias (malignancies derived from hematopoietic cells), and germ cell tumors (tumors derived from totipotent cells, in adults most often found in the testicle or ovary; in fetuses, babies and young children, most often found on the body midline, particularly at the tip of the tailbone), blastic tumors (a typically malignant tumor which resembles an immature or embryonic tissue) and the like. Examples of the types of neoplasms intended to be encompassed by the present invention include but are not limited to those neoplasms associated with cancers of neural tissue, blood forming tissue, breast, skin, bone, prostate, ovaries, uterus, cervix, liver, lung, brain, larynx, gallbladder, pancreas, rectum, parathyroid, thyroid, adrenal gland, immune system, head and neck, colon, stomach, bronchi, and/or kidneys. In particular embodiments, types and number of cancers that may be detected include, but are not limited to, blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like. In particular embodiments, the cancer is a hematological cancer, a sarcoma, or a prostate cancer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A sequencing system for identifying first and second breakpoints of a fusion gene associated with a disease or condition, comprising:

a communication interface configured to receive, over a communication network, genetic sequence read data from a sample of nucleic acid molecules from a subject generated by a nucleic acid sequencer, the genetic sequence read data comprising a paired-end sequencing reads 50 to 150 bases in length of at least 1 million polynucleotide molecules; and a computer in communication with the communication interface, the computer comprising one or more processors and a non-transitory machine-readable medium comprising instructions that, upon execution by the one or more processors, cause the computer to at least:

merge pairs of pair-end sequencing reads having a computed insert size less than a sum of lengths of the paired-end sequencing reads, thereby producing merged reads that minimize redundant alignment operations;

store the merged reads in a breakpoint read list data structure that retains a unique read identifier and clipping information for each merged read;

search a whole human reference genome for alignments of the merged reads wherein the search is configured to detect and preserve partial alignments indicating clipped portions, thereby producing mapped merged reads;

extract from the mapped merged reads, for each mapper merge read, one or more clipped portions, wherein a mapped read comprises:

a first clipped portion that aligns to a first region of the whole human reference genome and a second clipped portion that aligns to a second region of the whole human reference genome distinct from the first region, is identified as a fused read;

determine a respective candidate breakpoint pair for each fused read based on genomic positions at which the fused read is clipped, wherein the candidate breakpoint pair is stored in the breakpoint read list data structure and is linked to the unique read identifier;

determine a plurality of sets of fused reads, wherein each set of fused reads of the plurality of sets of fused reads comprises a plurality of the fused reads having a common candidate breakpoint pair;

generate one or more clusters of sets of fused reads, individual clusters of the one or more clusters including one or more sets of fused reads having candidate breakpoints within a predetermined genetic distance of one another and, for each cluster of the one or more clusters, (i) store a count of wild-type coverage crossing each candidate breakpoint, (ii) store a count of fused reads supporting each candidate breakpoint, and/or (iii) compute a metric comparing fused coverage to wild-type coverage;

select a final first breakpoint and a final second breakpoint for the fusion gene by applying at least one selection criterion to the candidate breakpoints in each cluster of the one or more of the clusters, wherein the at least one selection criterion requires at least one of:

(i) a minimum number of unique read identifiers and an observed reduction in false-positive alignments, or (ii) that the metric comparing fused coverage to wild-type coverage exceeds a threshold value, thereby reducing false-positive alignments and enabling increased specificity in fusion detection; and determine based on the final first breakpoint and the final second breakpoint of the fusion gene at least one of:

at least one of a diagnosis, a prognosis, or a risk of developing the disease or condition in the subject, a guide for treatment of the disease or condition, or a guide to preparation of a medicament for treatment of the disease or condition.

2. The system of claim 1, wherein individual sequencing reads comprise a first sequence corresponding to a polynucleotide molecule and one or more second sequences that correspond to adapters comprising barcode sequences.

3. The system of claim 2, wherein the nucleic acid sequencer is a high-throughput sequencer.

4. The system of claim 1, wherein the subject from which the sample of nucleic acid molecules was derived has cancer.

5. The system of claim 1, wherein the first and second breakpoints are independent of the individual sequencing reads in identity and are identified by a sign, a chromosome, and a position.

6. The system of claim 1, wherein the first region and the second region are located on different chromosomes or on different genes of the same chromosome.

7. The system of claim 1, wherein the predetermined genetic distance of the whole human reference genome includes no more than 5 nucleotides, no more than 10 nucleotides or no more than 25 nucleotides.

8. The system of claim 1, wherein the final first breakpoint of the fusion gene is a candidate breakpoint selected from the candidate breakpoints as having a greatest number of fused reads in a cluster of the one or more clusters and the final second breakpoint of the fusion gene is a candidate breakpoint selected from the candidate breakpoints as having a second greatest number of fused reads in the cluster.

9. The system of claim 1, wherein the non-transitory machine-readable medium comprises additional instructions that, upon execution by the one or more processors, perform additional operations comprising:

analyzing the sequencing reads included in the genetic sequence read data to determine a plurality of sequencing reads that are duplicates of respective sequencing reads included in the genetic sequence read data;

generating a master read sequence file, the master read sequence file including a subset of the sequencing reads that are not duplicates of the respective sequence reads included in the master read sequence file;

analyzing meta information included in the genetic sequence read data to determine one or more read identifiers for each of the plurality of sequencing reads that are duplicates of the respective sequencing reads; and generating a compressed file that includes the one or more read identifiers of the plurality of sequencing reads that are duplicates of the subset of the sequencing reads, the one or more read identifiers being indexed to the respective sequence reads included in the master read sequence file.

10. The system of claim 1, wherein the sample of nucleic acid molecules is obtained from an organism, such as from blood, serum, plasma, urine, cerebrospinal fluid, saliva, stool, lymph fluid, synovial fluid, cystic fluid, ascites, pleural effusion, amniotic fluid, chorionic villus sample, fluid from a preimplantation embryo, a placental sample, lavage and cervical vaginal fluid, interstitial fluid, a buccal swab sample, sputum, bronchial lavage, a Pap smear sample, or ocular fluid.

11. The system of claim 1, wherein the sequencing reads are derived from DNA molecules in the sample of nucleic acid molecules and the DNA molecules are isolated from a non cellular origin.

12. The system of claim 11, wherein the non-transitory machine-readable medium comprises additional computer-readable instructions that, upon execution by the one or more processors, perform additional operations comprising:

assigning a respective identifier to individual merged sequencing reads that uniquely identifies a DNA molecule in the sample of nucleic acid molecules.

13. The system of claim 12, wherein the non-transitory machine-readable medium comprises additional instructions that, upon execution by the one or more processors, perform additional operations comprising:

selecting clusters from the one or more clusters having at least one DNA molecule with sequencing reads representing both a Watson strand and a Crick strand.

14. The system of claim 11, wherein the DNA molecules comprise cell-free DNA.

15. The system of claim 12, wherein the non-transitory machine-readable medium comprises additional instructions that, upon execution by the one or more processors, perform additional operations comprising:

selecting clusters from the one or more clusters having more than one DNA molecule in the cluster.

* * * * *